(12) United States Patent
Beckman et al.

(10) Patent No.: US 11,793,584 B2
(45) Date of Patent: Oct. 24, 2023

(54) ROBOTIC SURGICAL INSTRUMENTS WITH RACK-BASED TRANSLATION AND FIRING TRANSMISSION

(71) Applicant: Cilag GmbH International, Zug (CH)

(72) Inventors: Andrew T. Beckman, Cincinnati, OH (US); Charles J. Scheib, Loveland, OH (US); Benjamin D. Dickerson, San Francisco, CA (US); Eric N. Johnson, Maineville, OH (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 207 days.

(21) Appl. No.: 17/153,998

(22) Filed: Jan. 21, 2021

(65) Prior Publication Data

US 2022/0226048 A1 Jul. 21, 2022

(51) Int. Cl.
| | |
|---|---|
| *A61B 34/30* | (2016.01) |
| *A61B 34/00* | (2016.01) |
| *A61B 17/32* | (2006.01) |
| *A61B 34/37* | (2016.01) |
| *A61M 25/01* | (2006.01) |
| *A61B 17/00* | (2006.01) |
| *A61B 50/13* | (2016.01) |
| *A61B 17/3211* | (2006.01) |

(52) U.S. Cl.
CPC ...... *A61B 34/30* (2016.02); *A61B 17/320016* (2013.01); *A61B 34/71* (2016.02); *A61B 34/37* (2016.02); *A61B 50/13* (2016.02); *A61B 2017/00991* (2013.01); *A61B 2017/32113* (2013.01); *A61B 2034/301* (2016.02); *A61B 2034/302* (2016.02); *A61B 2034/303* (2016.02); *A61B 2034/305* (2016.02); *A61M 25/0113* (2013.01)

(58) Field of Classification Search
CPC ......... A61B 34/30; A61B 34/71; A61B 34/35; A61B 2017/32113; A61B 2034/305
See application file for complete search history.

(56) References Cited

U.S. PATENT DOCUMENTS

| | | | |
|---|---|---|---|
| 2013/0211397 A1* | 8/2013 | Parihar | A61B 90/10 606/130 |
| 2013/0296886 A1* | 11/2013 | Green | B25J 15/04 606/130 |

(Continued)

*Primary Examiner* — Andrew M Tecco
(74) *Attorney, Agent, or Firm* — Vorys, Sater, Seymour and Pease LLP

(57) ABSTRACT

A robotic surgical tool includes a handle providing a first drive input and a second drive input, an elongate shaft extendable through the handle and having an end effector arranged at a distal end thereof, and a rack extending along a portion of the shaft and operatively coupled to a knife located at the end effector. Actuation of the first drive input transitions the rack between a locked configuration, where the rack is locked to the shaft, and a released configuration, where the rack is released from the shaft. Actuation of the second drive input with the rack in the locked configuration drives the rack and causes z-axis translation of the shaft through the handle. Actuation of the second drive input with the rack in the released configuration drives the rack relative to the shaft and thereby advances or retracts the knife at the end effector.

15 Claims, 25 Drawing Sheets

(56) References Cited

U.S. PATENT DOCUMENTS

| | | | |
|---|---|---|---|
| 2014/0276720 A1* | 9/2014 | Parihar | A61B 18/1447 606/130 |
| 2014/0276723 A1* | 9/2014 | Parihar | A61B 17/07207 606/33 |
| 2014/0276761 A1* | 9/2014 | Parihar | A61B 18/12 606/34 |
| 2019/0343525 A1* | 11/2019 | Shelton, IV | A61B 17/07207 |
| 2021/0015572 A1* | 1/2021 | Gomez | A61B 34/35 |
| 2021/0022815 A1* | 1/2021 | Abbott | A61B 34/71 |

* cited by examiner

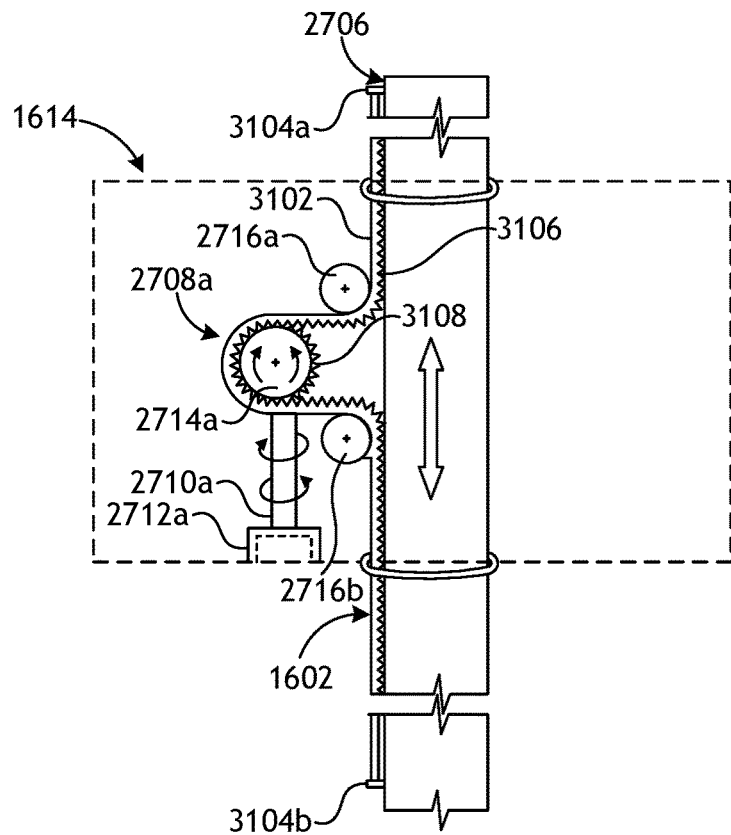
FIG. 31
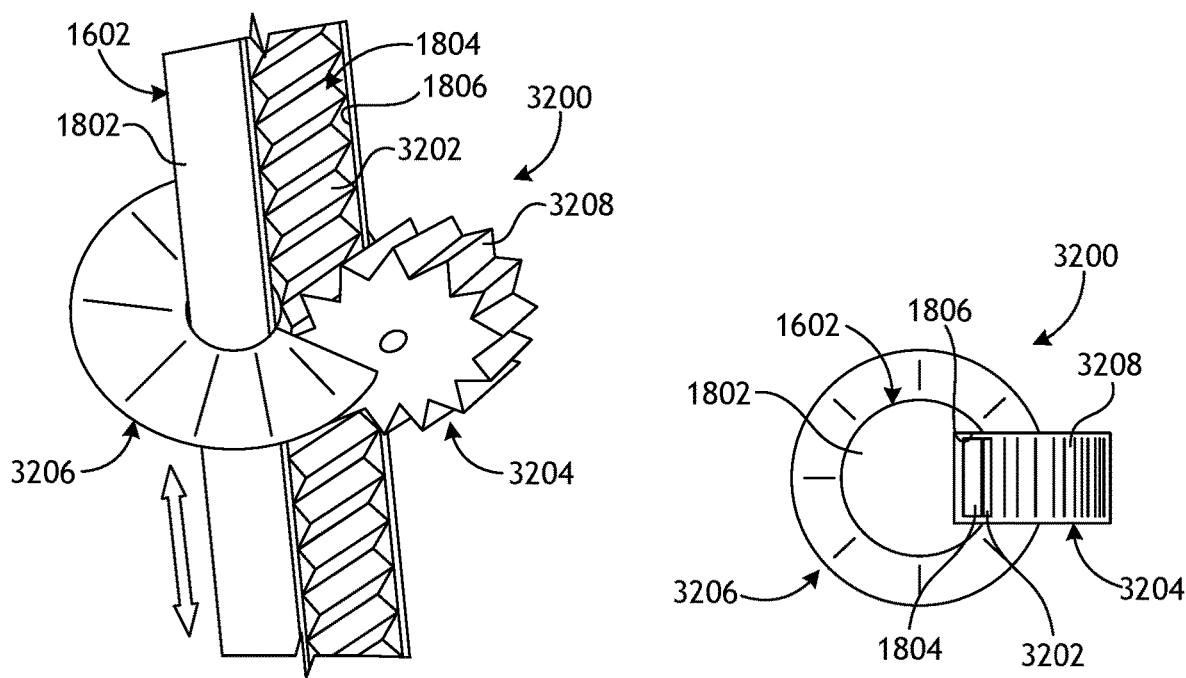
FIG. 32A
FIG. 32B

ROBOTIC SURGICAL INSTRUMENTS WITH RACK-BASED TRANSLATION AND FIRING TRANSMISSION

TECHNICAL FIELD

The systems and methods disclosed herein are directed to robotic surgical tools and, more particularly to, robotic surgical instruments that incorporate a rack-based translation and firing transmission system.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving drive cables, rods, and/or other mechanical mechanisms causes the end effector to articulate to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a handle providing a first drive input and a second drive input, an elongate shaft extendable through the handle and having an end effector arranged at a distal end thereof, and rack extending along a portion of the shaft and operatively coupled to a knife located at the end effector, wherein actuation of the first drive input transitions the rack between a locked configuration, where the rack is locked to the shaft, and a released configuration, where the rack is released from the shaft, wherein actuation of the second drive input with the rack in the locked configuration drives the rack and causes z-axis translation of the shaft through the handle, and wherein actuation of the second drive input with the rack in the released configuration drives the rack relative to the shaft and thereby advances or retracts the knife at the end effector. In a further embodiment, the robotic surgical tool further includes an actuation system housed within the handle and including a shifting mechanism operatively coupled to the first drive input such that actuation of the first drive input transitions the rack between the locked configuration and the released configuration, and a capstan coupled to the second drive input and including a drive gear engageable with a gear train that intermeshes with the rack. In another further embodiment, the robotic surgical tool further includes a rack locking assembly arranged at a proximal end of the shaft and including a latch pivotably coupled to the shaft and engageable with the rack, and a drive cable extending from the shifting mechanism and fixed to the latch, wherein transitioning the actuation system to the second configuration places tension on the drive cable and thereby pivots the latch from a locked position, where the latch secures the rack to the shaft, to a released position, where the latch is released from the rack and allows the rack to move relative to the shaft. In another further embodiment, the latch is spring biased to the locked position. In another further embodiment, a distal end of the drive cable is anchored to the shaft distal to the handle and the drive cable extends through one or more pulleys included in the shifting mechanism, and wherein actuation of the first drive input shifts the shifting mechanism and thereby draws in or pays out a portion of the drive cable. In another further embodiment, the robotic surgical tool further includes a shaft locking mechanism operatively coupled to a third drive input of the handle, wherein actuation of the third drive input causes the shaft locking mechanism to engage and prevent the shaft from moving in z-axis translation. In another further embodiment, the shaft locking mechanism comprises first and second caliper actuating arms pivotably coupled to each other at a first end and engageable with the third drive input at a second end, and wherein actuation of the third drive input forces the first and second caliper actuating arms into lateral binding engagement with the shaft.

Embodiments disclosed herein further include a robotic surgical tool that includes a handle providing a first drive input, a second drive input, and a third drive input, an elongate shaft extendable through the handle and having an end effector arranged at a distal end thereof, a rack extending along a portion of the shaft and operatively coupled to a knife located at the end effector, an actuation system housed within the handle and including a shifting mechanism operatively coupled to the first drive input such that actuation of the first drive input transitions the actuation system between a first configuration, where the rack is locked to the shaft, and a second configuration, where the rack is released from the shaft, a first capstan coupled to the second drive input and including a first drive gear engageable with a gear train that intermeshes with the rack when the actuation system is in the first configuration, and a second capstan coupled to the third drive input and including a second drive gear engageable with the gear train when the actuation system is in the second configuration, wherein actuation of the second drive input with the actuation system in the first configuration drives the rack and causes z-axis translation of the shaft through the handle, and wherein actuation of the third drive input with the actuation system in the second configuration drives the rack relative to the shaft and thereby advances or retracts the knife at the end effector. In a further embodiment, the robotic surgical tool further includes a rack locking assembly arranged at a proximal end of the shaft and including a latch pivotably coupled to the shaft and engageable with the rack, and a drive cable extending from the shifting mechanism and fixed to the latch, wherein transitioning the actuation system to the second configuration places tension on the drive cable and thereby pivots the latch from a locked position, where the latch secures the rack to the shaft, to a released position, where the latch is released from the rack and allows the rack to move relative to the shaft. In another further embodiment, the latch is spring biased to the locked position. In another further embodiment, a distal end of the drive cable is anchored to the shaft distal to the handle and the drive cable extends through one or more pulleys included in the shifting mechanism, and wherein actuation of the first drive input shifts the shifting mechanism and thereby draws in or pays out a portion of the drive cable. In another further embodiment, the robotic surgical tool further includes a shaft locking mechanism operatively coupled to a fourth drive input of the handle, wherein actuation of the fourth drive input causes the shaft locking mechanism to engage and prevent the shaft from moving in z-axis translation. In another further embodiment, the shaft locking mechanism comprises first and second caliper actuating arms pivotably coupled to each other at a first end and engageable with the fourth drive input at a second end, and wherein actuation of the fourth drive input forces the first and second caliper actuating arms into lateral binding engagement with the shaft. In another further embodiment, the robotic surgical tool further includes a first driven gear mounted to an axle and engageable with the first drive gear, a second driven gear mounted to the axle and engageable with the second drive gear, and a clutch interposing the first and second drive gears and laterally movable with the shifting mechanism between the first and second driven gears, wherein the clutch engages a first clutch interface at the first driven gear when the actuation system is in the first configuration and thereby allows the first drive gear to drive the rack via the gear train, and wherein the clutch engages a second clutch interface at the second driven gear when the actuation system is in the second configuration and thereby allows the second drive gear to drive the rack via the gear train. In another further embodiment, the clutch includes a spool engageable with a pin provided by the shifting mechanism, and wherein transitioning the actuation system between the first and second configurations moves the clutch between the first and second clutch interfaces via the engaged spool and pin.

Embodiments disclosed herein further include a method of operating a robotic surgical tool, the method including arranging a robotic surgical tool adjacent a patient, the robotic surgical tool including an elongate shaft extending through a handle and having an end effector arranged at a distal end thereof, the handle providing a first drive input and a second drive input, a rack extending along a portion of the shaft and operatively coupled to a knife located at the end effector, and an actuation system housed within the handle and including a shifting mechanism operatively coupled to the first drive input, a capstan coupled to the second drive input and including a drive gear engageable with a gear train that intermeshes with the rack. The method further includes actuating the first drive input and thereby transitioning the actuation system to a first configuration where the rack is locked to the shaft, actuating the second drive input with the actuation system in the first configuration and thereby rotating the capstan and causing z-axis translation of the shaft through the handle, actuating the first drive input and thereby transitioning the actuation system to a second configuration where the rack is released from the shaft, and driving the rack relative to the shaft with the actuation system in the second configuration and thereby advancing or retracting the knife at the end effector. In a further embodiment, driving the rack relative to the shaft comprises actuating the second drive input with the actuation system in the second configuration and thereby driving the rack relative to the shaft to advance or retract the knife at the end effector. In another further embodiment, the robotic surgical tool further includes a rack locking assembly arranged at a proximal end of the shaft and including a latch pivotably coupled to the shaft and engageable with the rack, and a drive cable extending from the shifting mechanism and fixed to the latch, and wherein actuating the first drive input and thereby transitioning the actuation system to the second configuration comprises shifting the shifting mechanism and thereby placing tension on the drive cable, and pivoting the latch from a locked position, where the latch secures the rack to the shaft, to a released position, where the latch is released from the rack and allows the rack to move relative to the shaft. In another further embodiment, the robotic surgical tool further a shaft locking mechanism operatively coupled to a third drive input of the handle, the method further comprising actuating the third drive input when the actuation system is in the second configuration and thereby engaging the shaft with the shaft locking mechanism and preventing the shaft from moving in z-axis translation, and actuating the third drive input when the actuation system is in the first configuration and thereby disengaging the shaft with the shaft locking mechanism and allowing the shaft to move in z-axis translation. In another further embodiment, the capstan is a first capstan, the drive gear is a first drive gear, and the robotic surgical tool further includes a third drive input provided by the handle, and a second capstan coupled to the third drive input and including a second drive gear engageable with the gear train when the actuation system is in the second configuration, and wherein driving the rack relative to the shaft with the actuation system in the second configuration comprises actuating the third drive input with the actuation system in the second configuration and thereby driving the rack relative to the shaft to advance or retract the knife at the end effector. In another further embodiment, the robotic surgical tool further includes a rack locking assembly arranged at a proximal end of the shaft and including a latch pivotably coupled to the shaft and engageable with the rack, and a drive cable extending from the shifting mechanism and fixed to the latch, and wherein actuating the first drive input and thereby transitioning the actuation system to the second configuration comprises shifting the shifting mechanism and thereby placing tension on the drive cable, and pivoting the latch from a locked position, where the latch secures the rack to the shaft, to a released position, where the latch is released from the rack and allows the rack to move relative to the shaft. In another further embodiment, the robotic surgical tool further includes a first driven gear mounted to an axle and engageable with the first drive gear, a second driven gear mounted to the axle and engageable with the second drive gear, and a clutch interposing the first and second drive gears and laterally movable with the shifting mechanism between the first and second driven gears, and wherein the method further comprises engaging the clutch at a first clutch interface at the first driven gear when the actuation system is in the first configuration and thereby allowing the first drive gear to drive the rack via the gear train, and engaging the clutch at a second clutch interface at the second driven gear when the actuation system is in the second configuration and thereby allowing the second drive gear to drive the rack via the gear train.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 31 is an enlarged side schematic view of another embodiment of the handle of FIGS. 16-17, according to one or more additional embodiments of the present disclosure.

FIGS. 32A and 32B are isometric side and top views, respectively, of an example seal system that may be incorporated into one or more of the presently disclosed embodiments.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
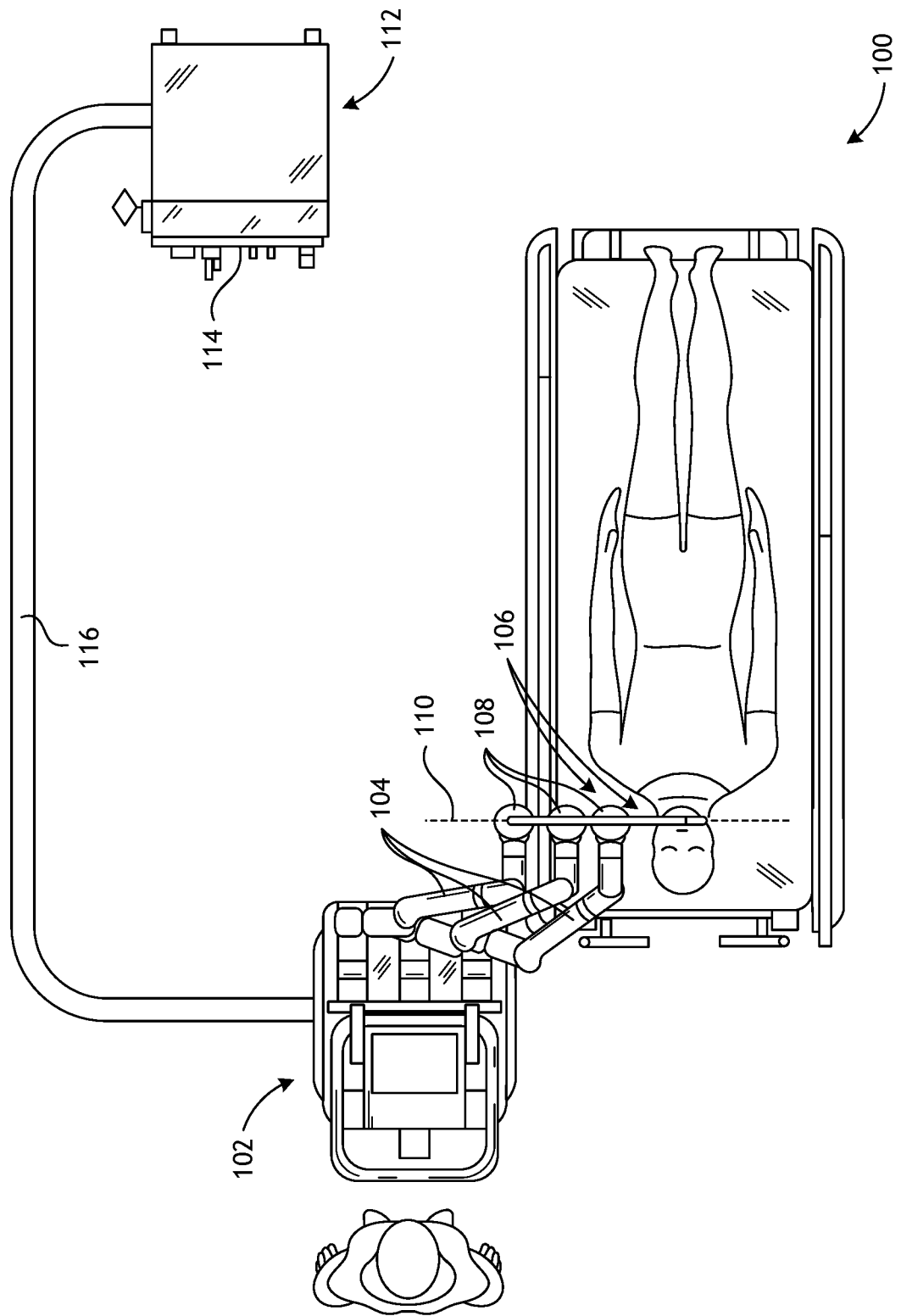
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
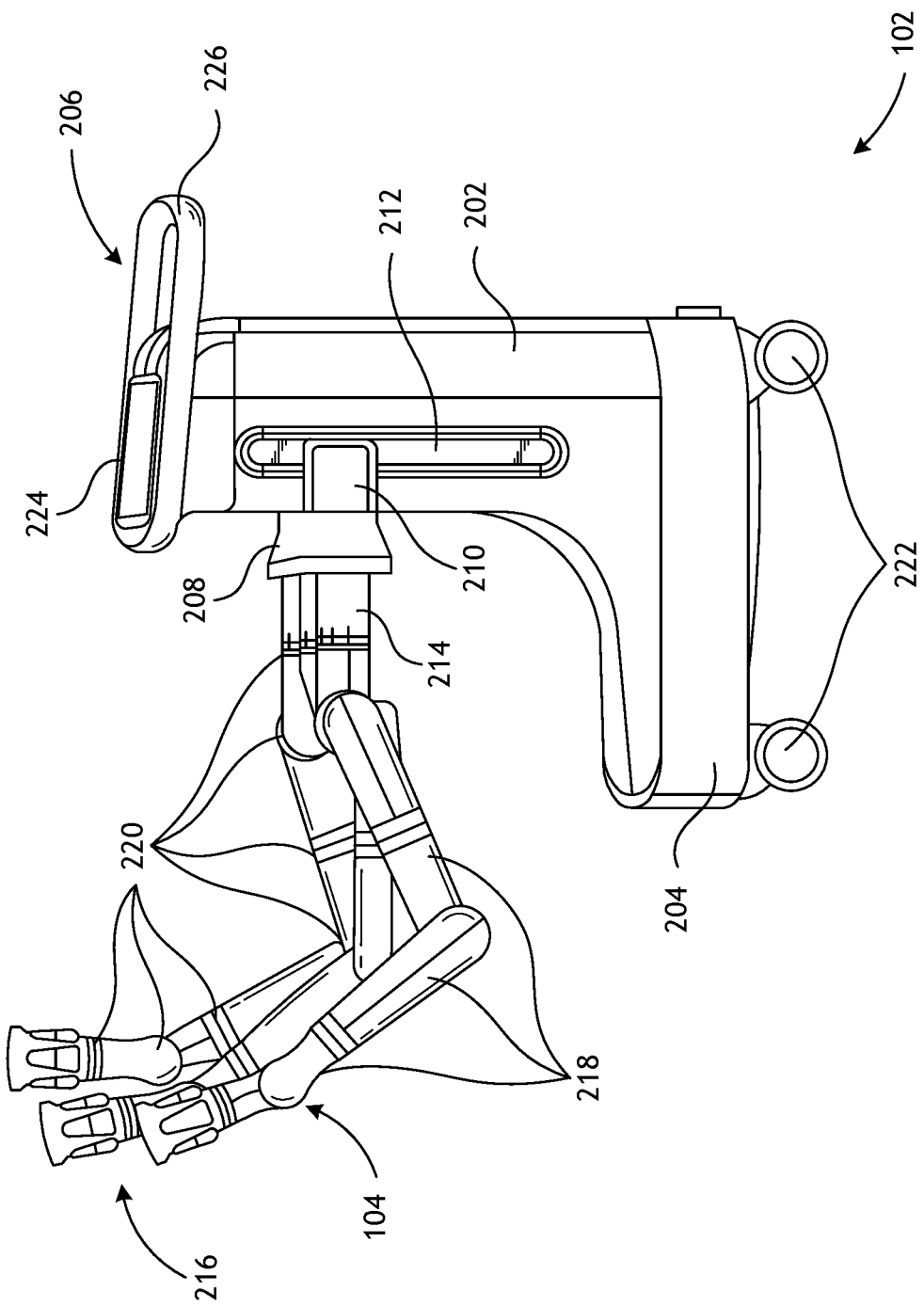
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
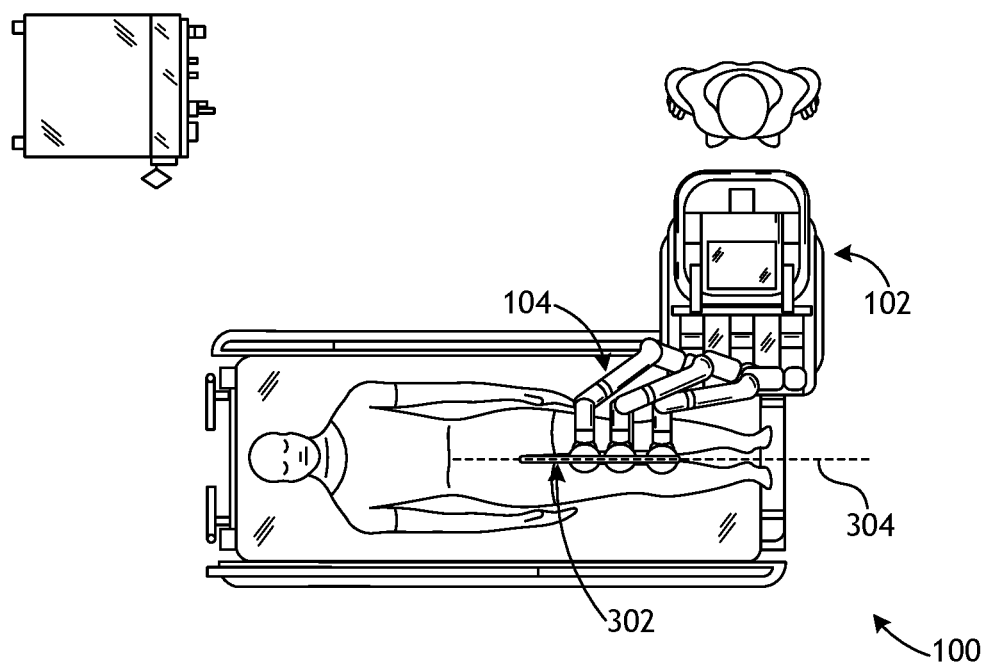
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
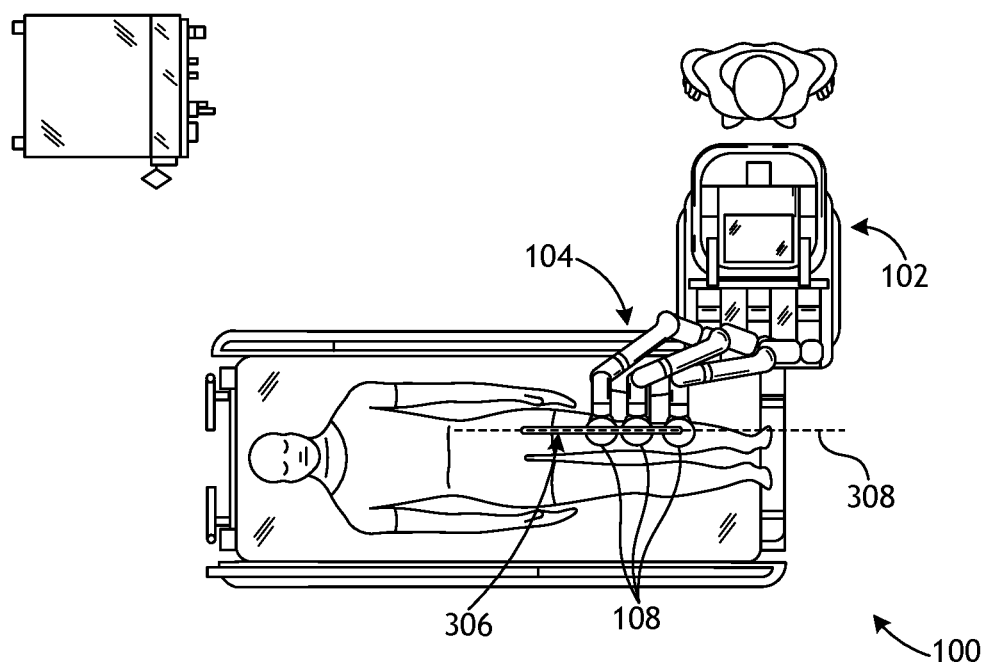
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
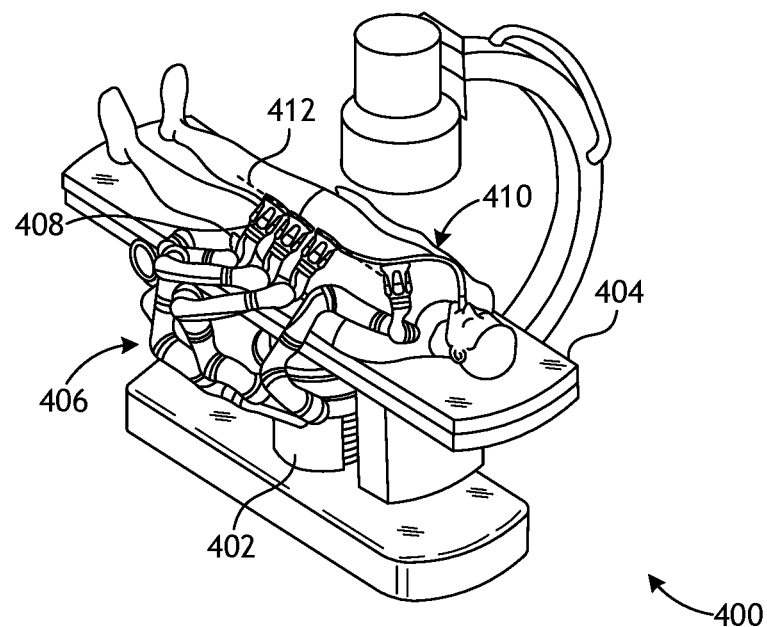
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
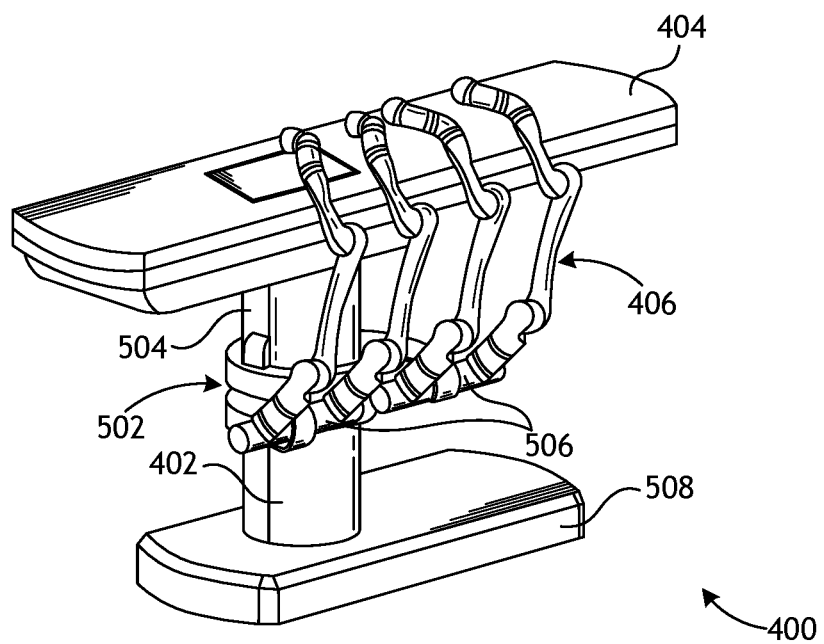
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
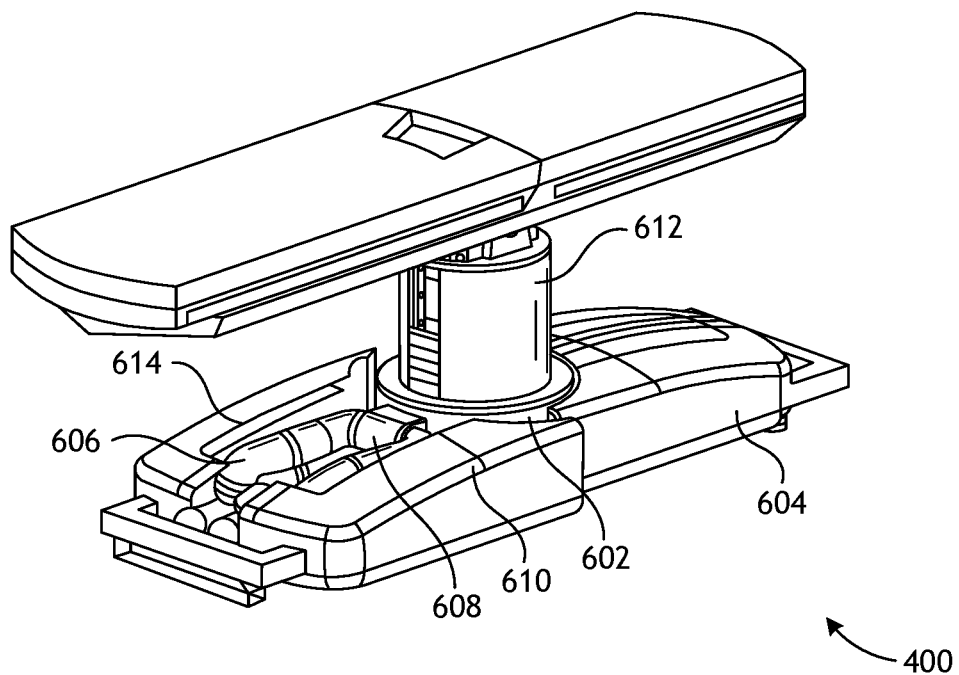
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
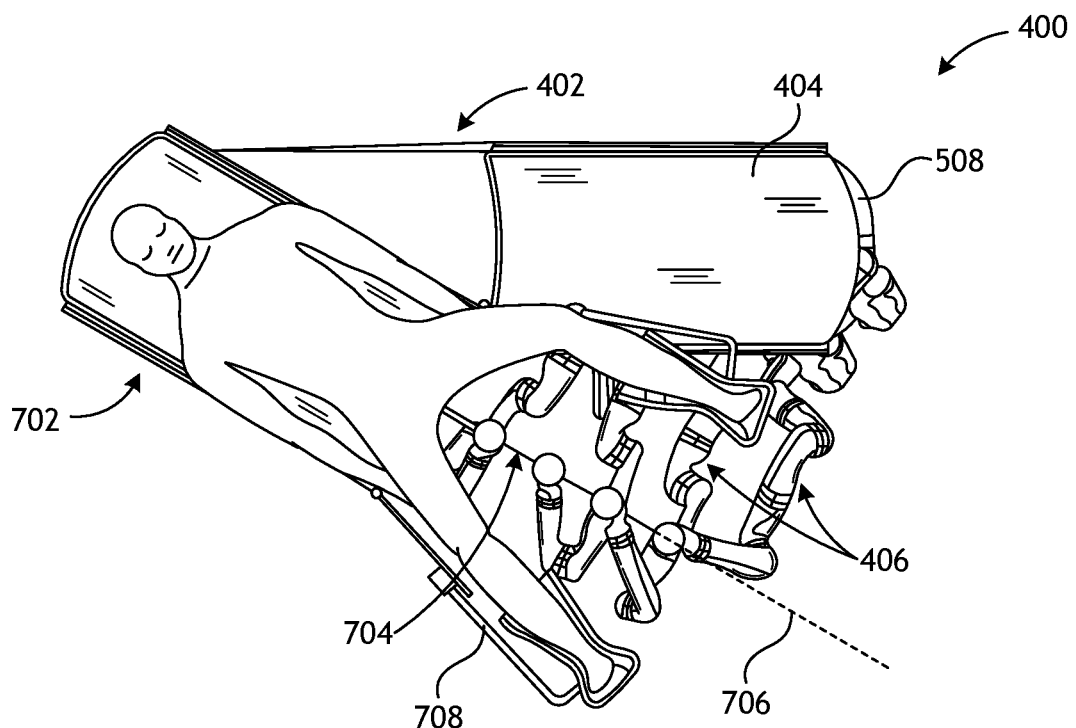
FIG. 7A illustrates an embodiment of a table-based robotic system configured for a ureteroscopy procedure.
Figure 7B:
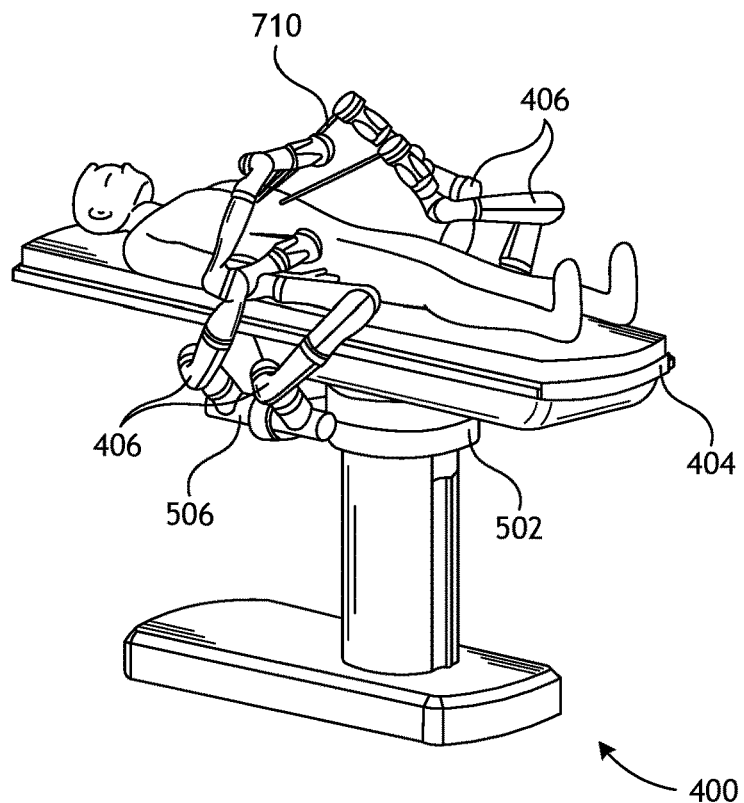
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
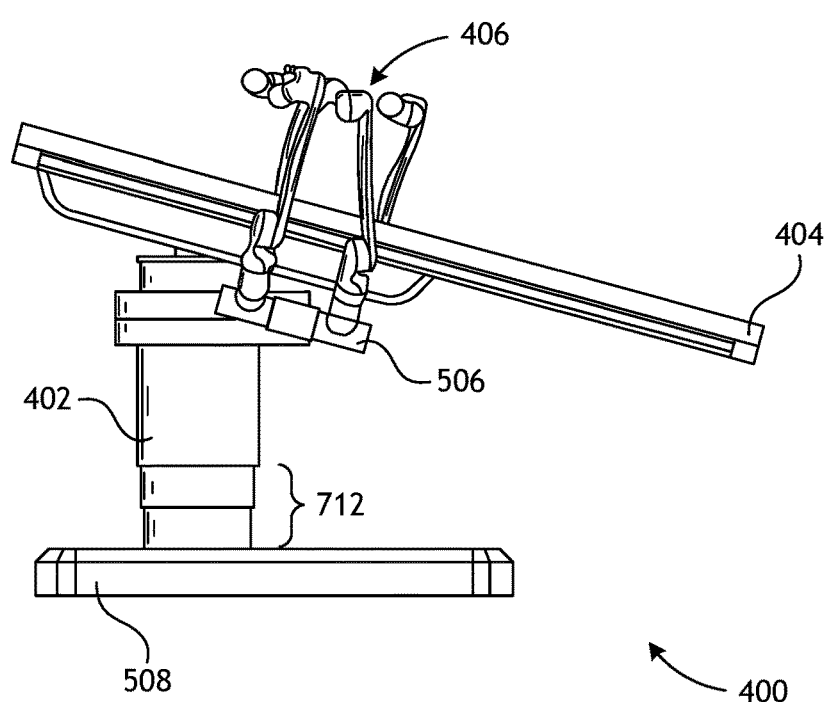
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
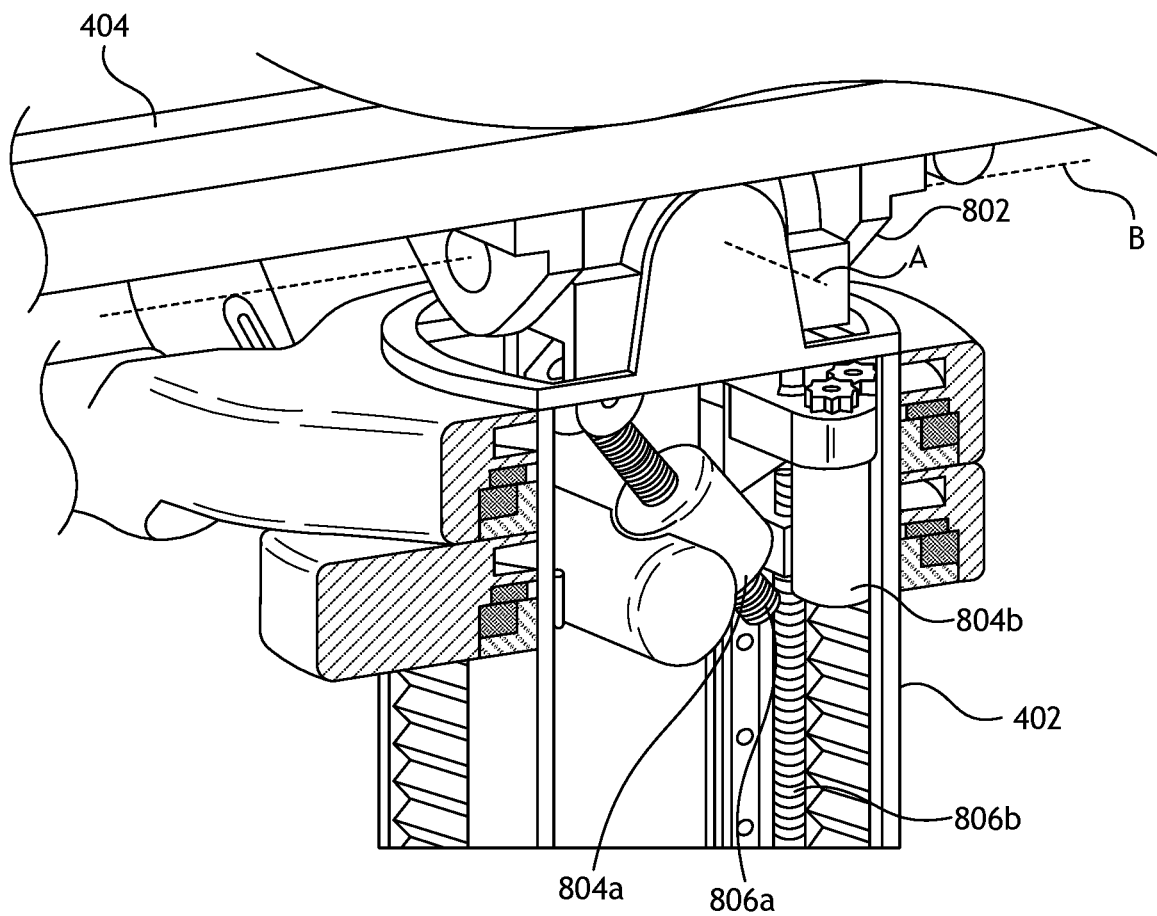
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
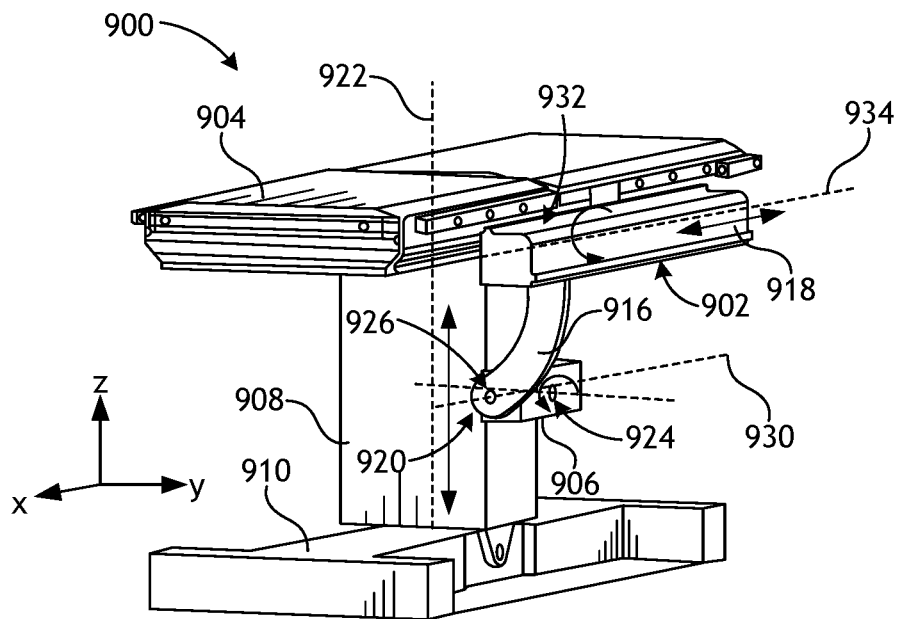
FIG. 9A illustrates an alternative embodiment of a table-based robotic system.
Figure 9B:
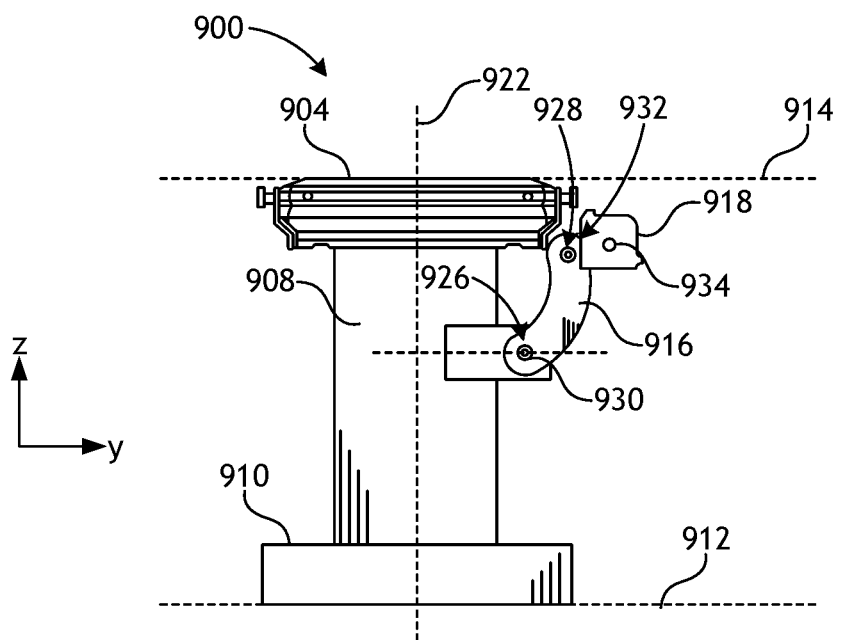
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
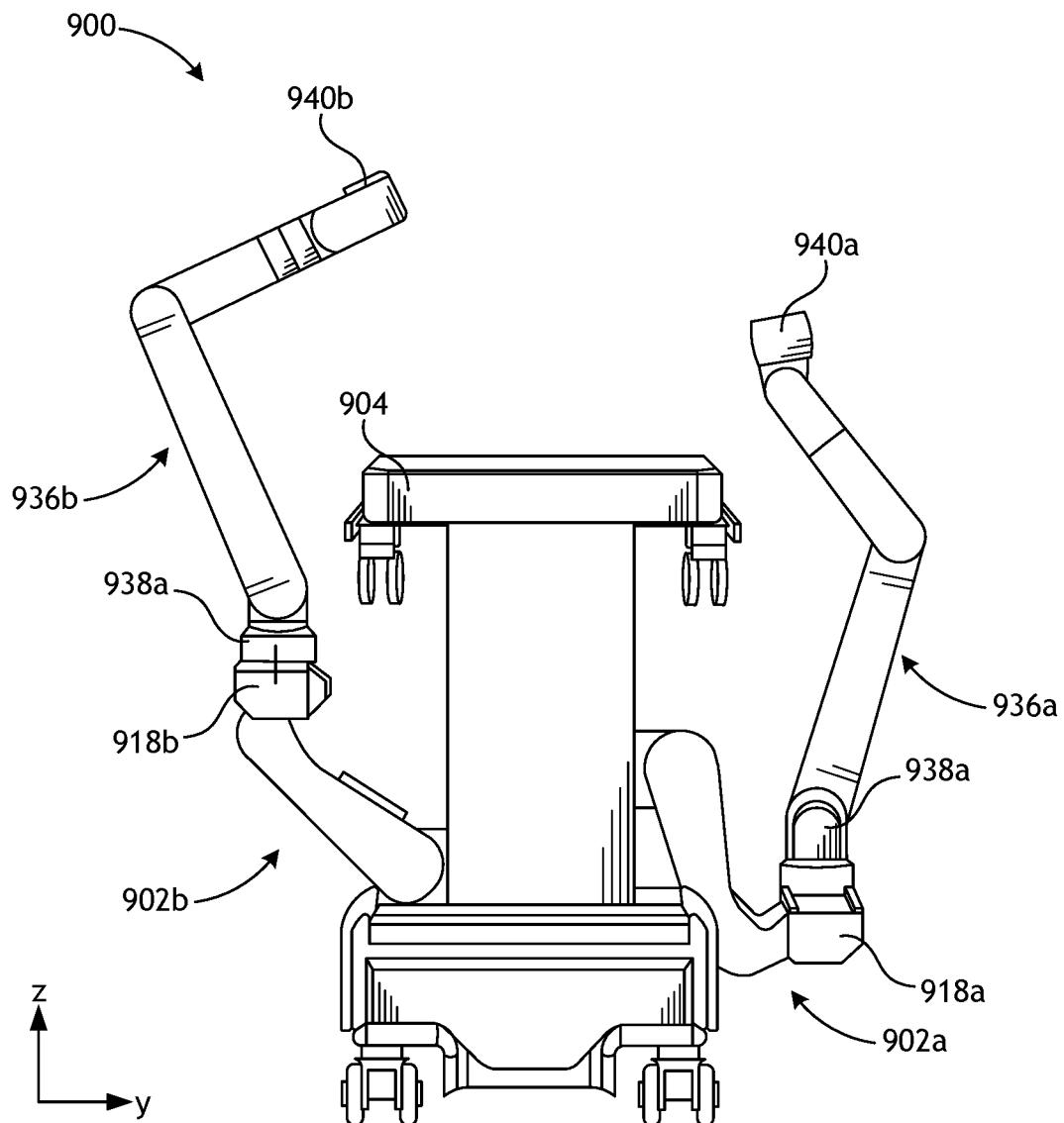
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
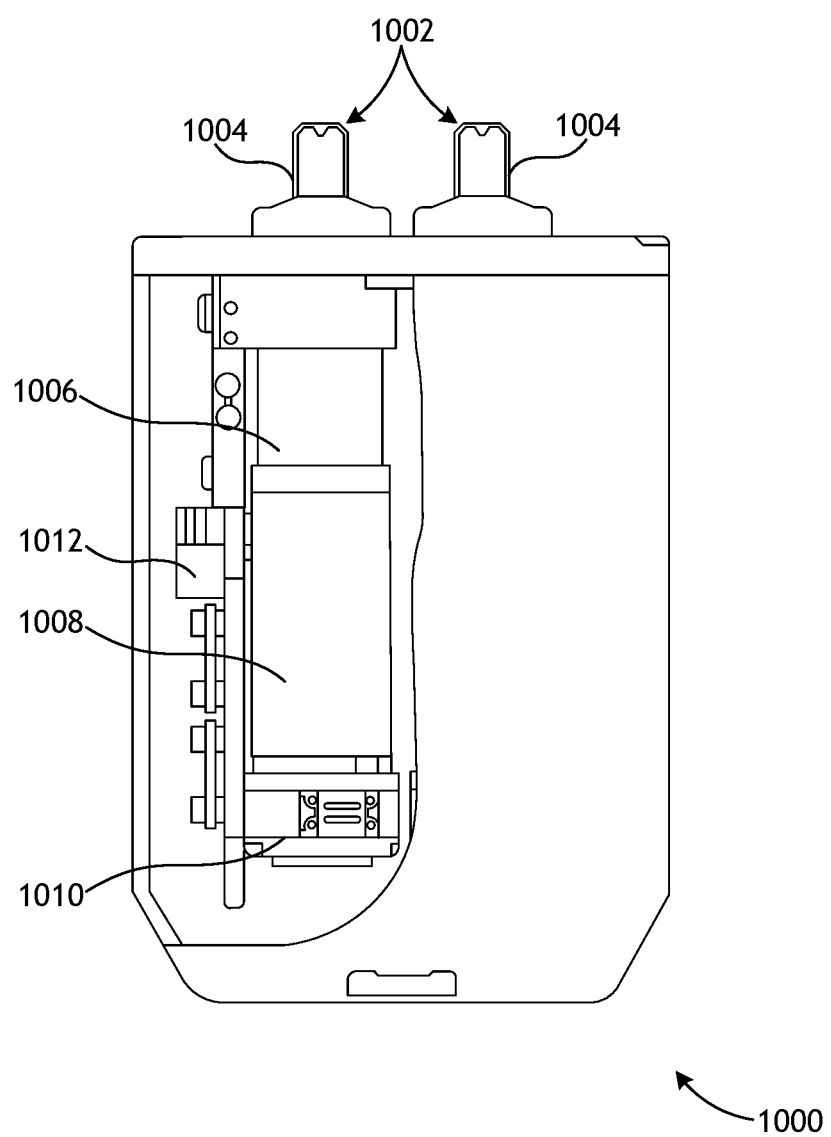
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
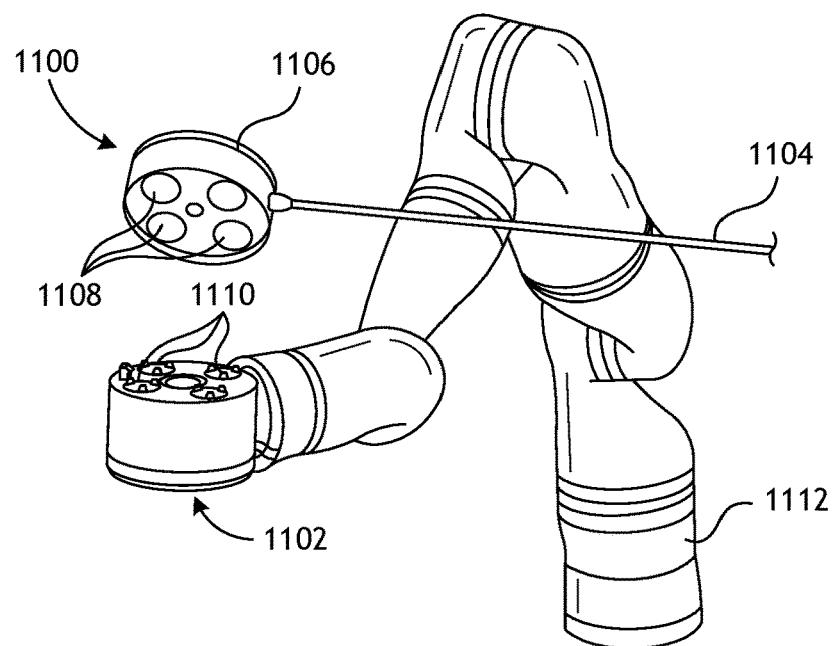
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
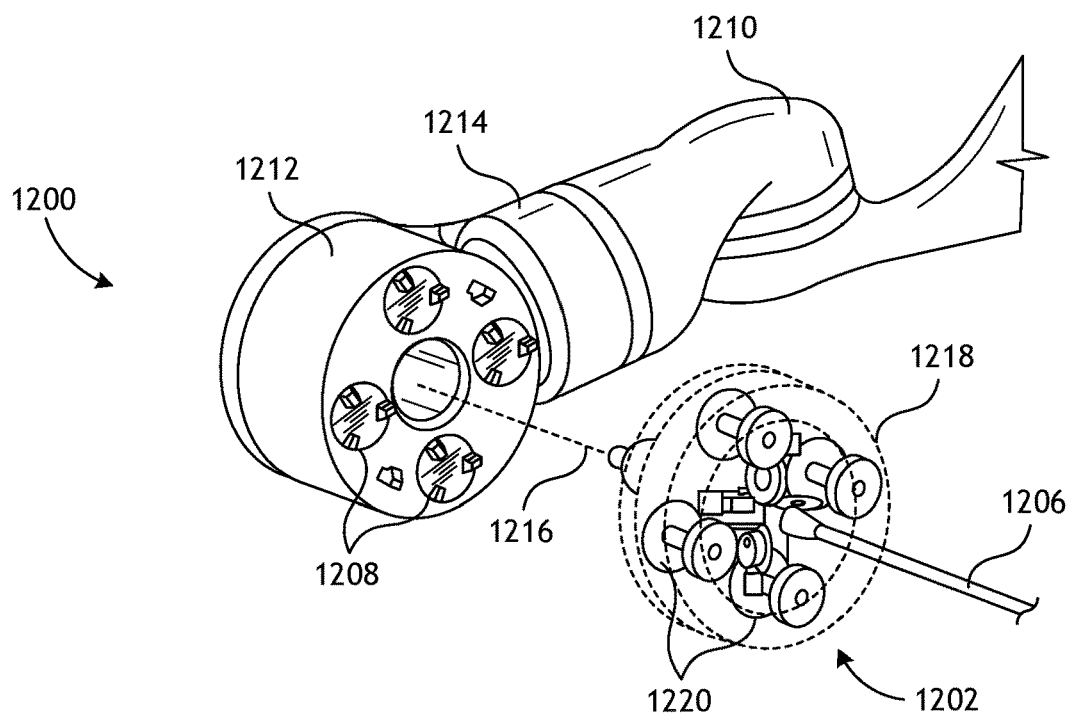
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
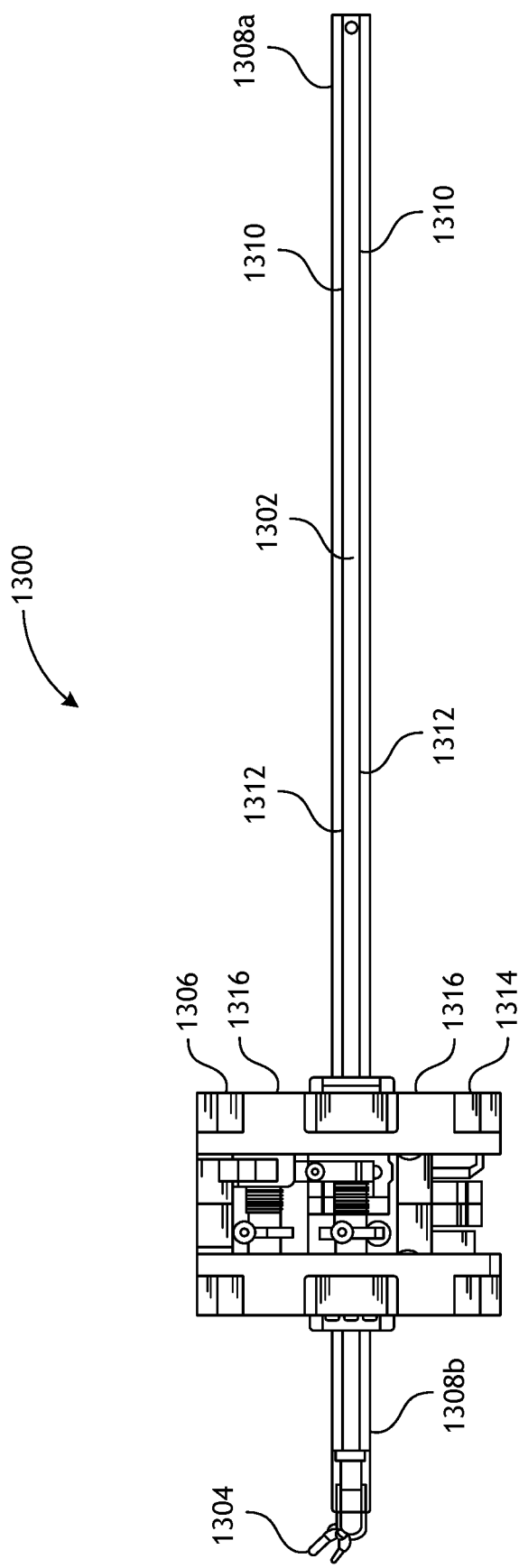
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
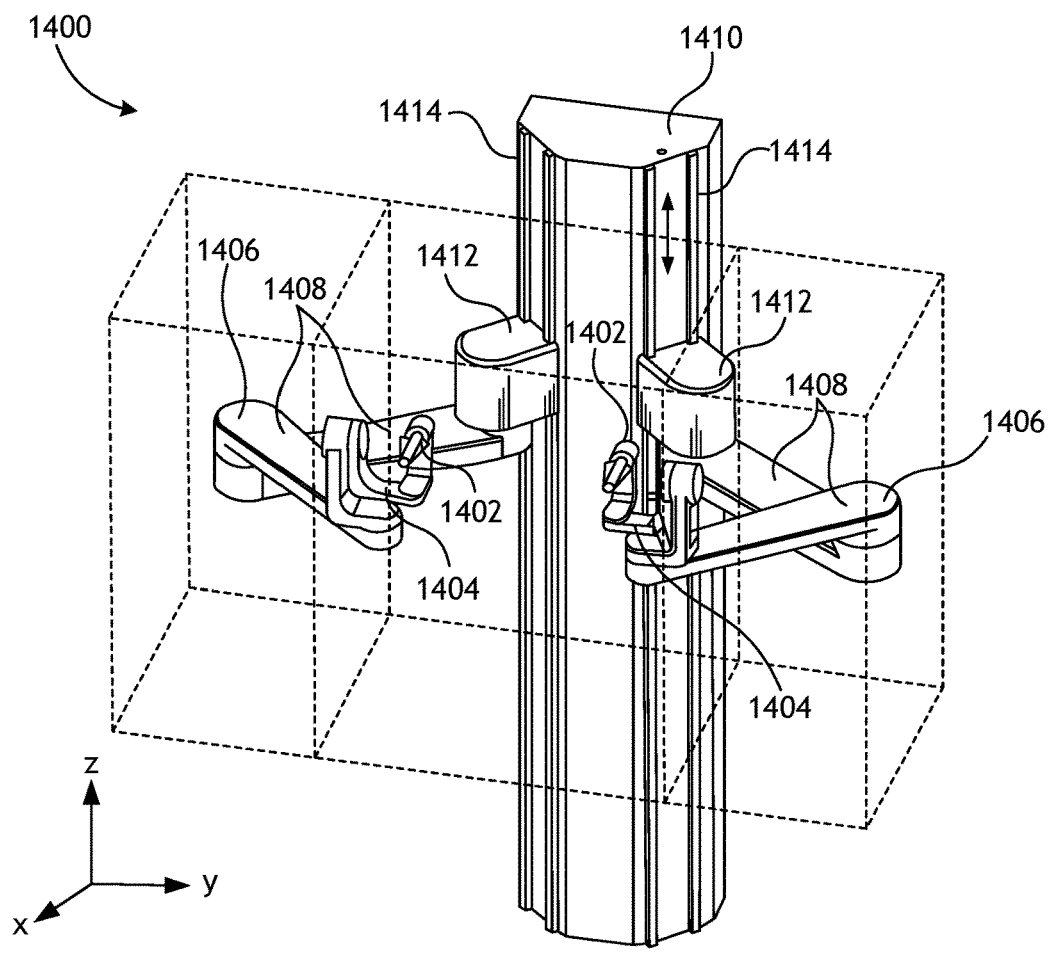
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
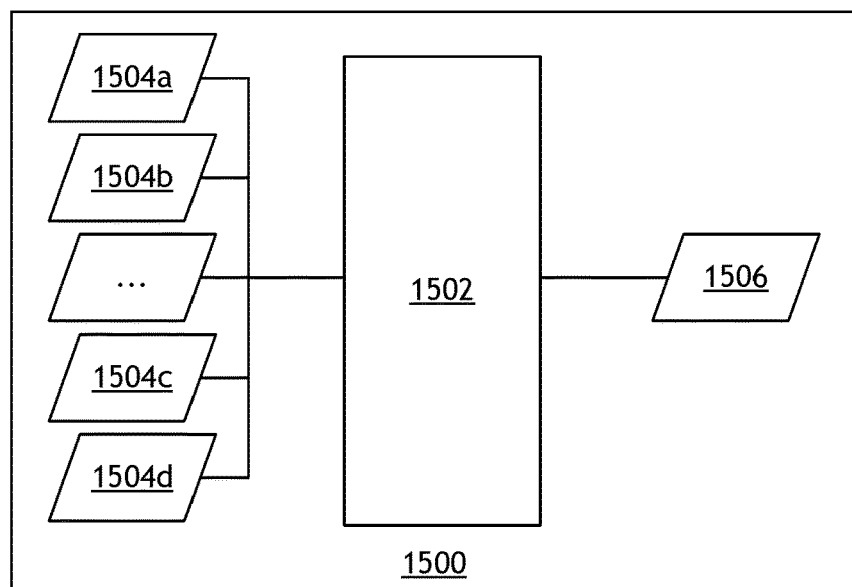
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description.

Embodiments of this disclosure relate to rack-based robotic surgical tools capable of facilitating z-axis translation of a shaft and actuation of a knife at an end effector, depending on the configuration of a shifting mechanism. At least one robotic surgical tool includes a handle providing a first drive input and a second drive input, an elongate shaft extendable through the handle and having an end effector arranged at a distal end thereof, and rack extending along a portion of the shaft and operatively coupled to a knife located at the end effector, wherein actuation of the first drive input transitions the rack between a locked configuration, where the rack is locked to the shaft, and a released configuration, where the rack is released from the shaft, wherein actuation of the second drive input with the rack in the locked configuration drives the rack and causes z-axis translation of the shaft through the handle, and wherein actuation of the second drive input with the rack in the released configuration drives the rack relative to the shaft and thereby advances or retracts the knife at the end effector.

Figure 16:
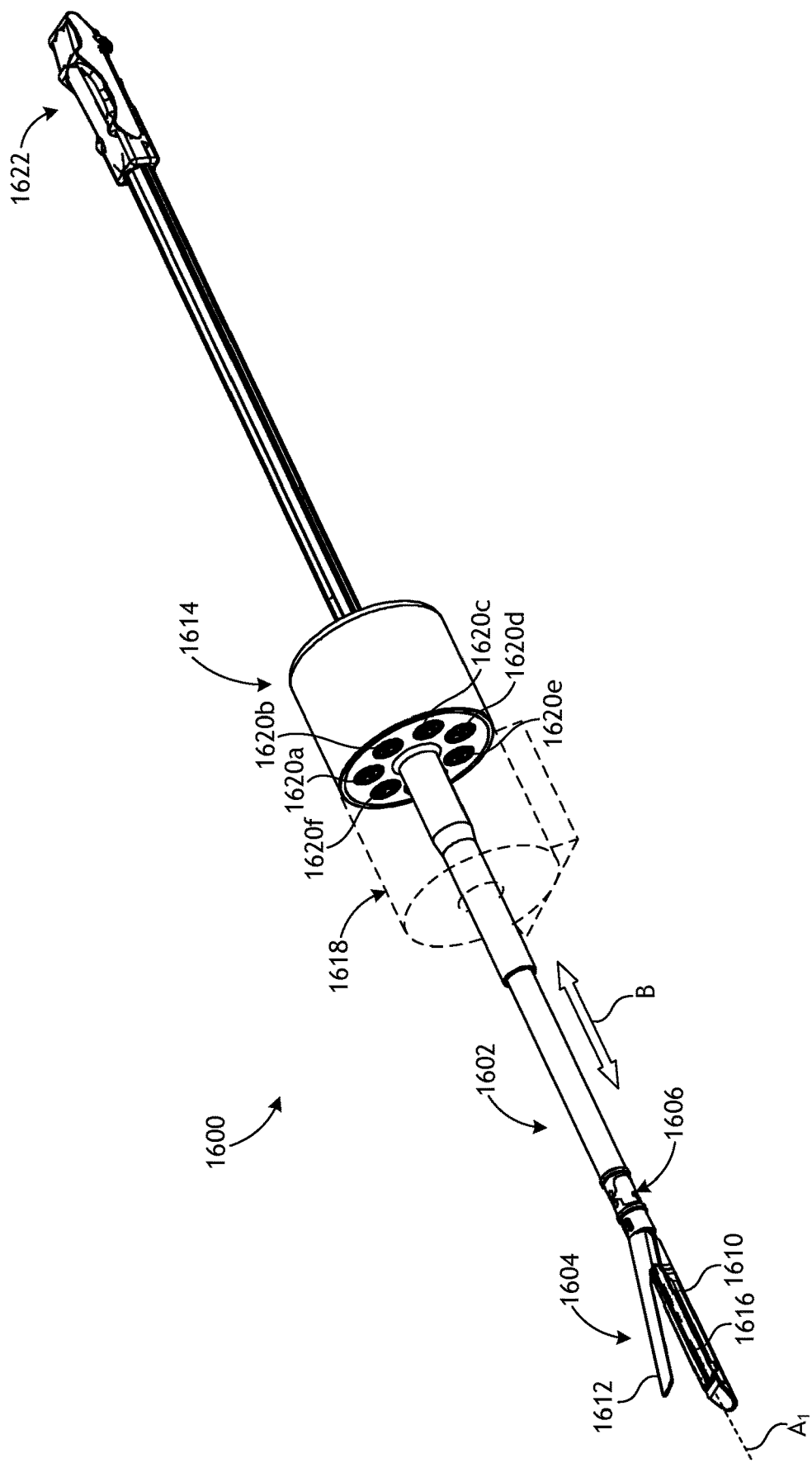
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610 and 1612 configured to move (articulate) between open and closed positions. Alternatively, the end effector 1604 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 may be rotatable (pivotable) relative to the first jaw 1610 to actuate the end effector 1604 between an open, unclamped position and a closed, clamped position. In other embodiments, however, the first jaw 1610 may move (rotate) relative to the second jaw 1612 to move the jaws 1610, 1612 between open and closed positions. In yet other embodiments, both jaws 1610, 1612 may simultaneously move between open and closed positions (e.g., bifurcating jaws).

In the illustrated example, the first jaw 1610 is referred to as a "cartridge" or "channel" jaw, and the second jaw 1612 is referred to as an "anvil" jaw. The first jaw 1610 includes a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the centerline of the end effector 1604 is substantially aligned with the longitudinal axis $A_1$ of the shaft 1602, such that the end effector 1604 is at a substantially zero angle relative to the shaft 1602. In the articulated position, the centerline of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1614, and the shaft 1602 extends longitudinally through the handle 1614. The handle 1614 houses various actuation systems designed to operate the surgical tool. At least one actuation system, for example, may be designed to move the shaft 1602 relative to the handle 1614 (i.e., z-axis translation), as indicated by the arrows B, and thereby advance or retract the end effector 1604. Other actuation systems may be designed to facilitate articulation of the wrist 1606 and actuation (operation) of the end effector 1604 (e.g., clamping, firing, rotation, articulation, energy delivery, etc.). Some of the actuation systems and mechanisms housed within the handle 1614 are actuatable to move (translate) a plurality of drive members (mostly obscured in FIG. 16) that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally, the knife transects any tissue grasped between the opposing jaws 1610, 1612. Moreover, as the knife advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As will be appreciated, however, the end effector 1604 may be replaced with any of the other types of end effectors mentioned herein, and in those cases actuating the end effector 1604 may entail a variety of other actions or movements, without departing from the scope of the disclosure. For example, in some embodiments, the end effector 1604 may be replaced with a vessel sealer and actuating such an end effector 1604 may further entail triggering energy delivery (e.g., RF energy) to cauterize and/or seal tissue or vessels.

The handle 1614 provides or otherwise includes various coupling features (not shown) that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the actuation systems and mechanisms housed within the handle 1614 and thereby operate the surgical tool 1600. In the illustrated embodiment, the handle 1614 includes a first drive input 1620a, a second drive input 1620b, a third drive input 1620c, a fourth drive input 1620d, a fifth drive input 1620e, and a sixth drive input 1620f While six drive inputs 1620a-f are depicted, more or less than six may be included in the handle 1614 depending on the application, and without departing from the scope of the disclosure. Each drive input 1620a-f may be matable with a corresponding drive output (not shown) of the instrument driver 1618 such that movement (rotation) of a given drive output correspondingly moves (rotates) the associated drive input 1620a-f and thereby causes various operations of the surgical tool 1600.

In some embodiments, actuation of the first drive input 1620a may cause the knife to fire at the end effector 1604, thus advancing or retracting the knife, depending on the rotational direction of the first drive input 1620a. Actuation of the third drive input 1620c may cause the shaft 1602 to move (translate) relative to the handle 1614 along the longitudinal axis $A_1$, depending on the rotational direction of the third drive input 1620c. In some embodiments, and as discussed in more detail herein, actuation of the second drive input 1620b may shift operation or activation within the handle 1614 between the first and third drive inputs 1620a,c. Consequently, actuation of the second drive input 1620b will dictate whether the knife is fired or whether the shaft 1602 is moved (translated). Actuation of the fourth drive input 1620d may lock and unlock z-axis translation of the shaft 1602, and actuation of the fifth drive input 1620e may cause articulation of the end effector 1604 at the wrist 1606. Lastly, actuation of the sixth drive input 1620f may cause the jaws 1610, 1612 to open or close, depending on the rotational direction of the sixth drive input 1620f. In some embodiments, for example, actuation of the sixth drive input 1620f may operate a toggle mechanism 1622 arranged at the proximal end of the shaft 1602, and actuation of the toggle mechanism 1622 may cause the jaws 1610, 1612 to open and close.

Figure 17:
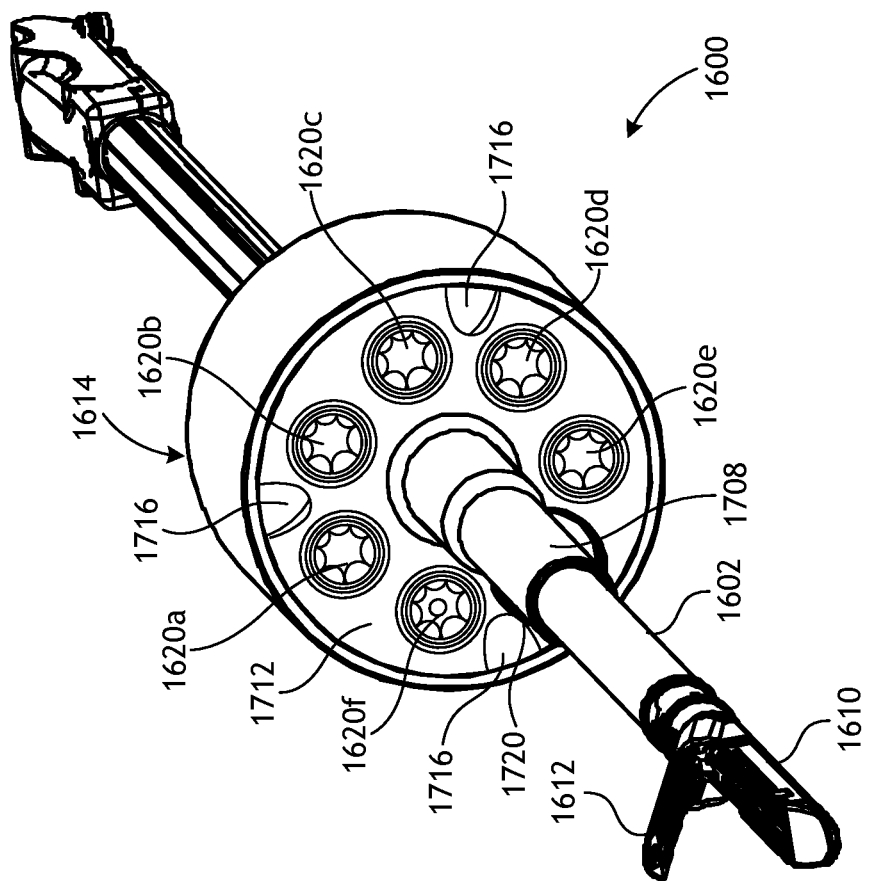
FIG. 17 depicts separated isometric end views of the instrument driver and the surgical tool of FIG. 16.
Figure 17:
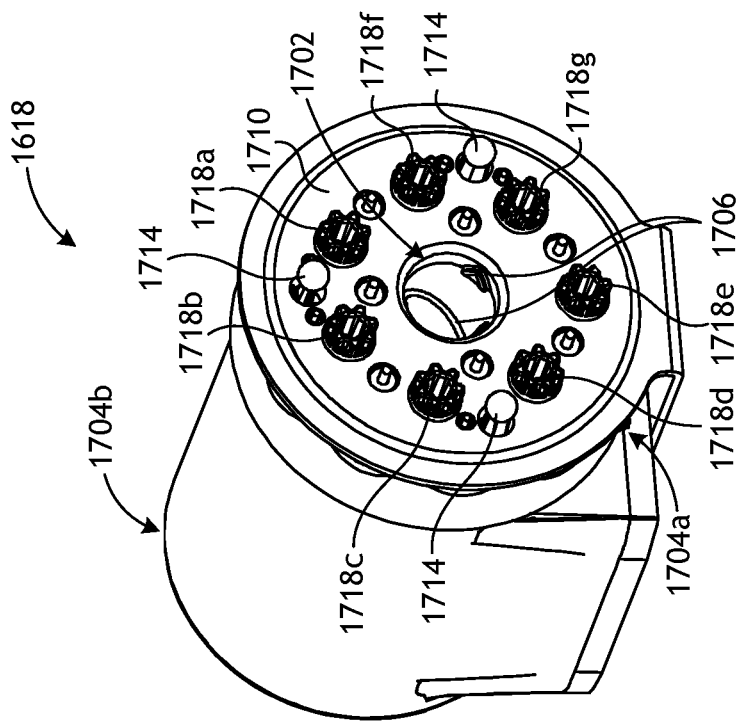

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704a,b. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704a of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620a-f provided at the distal end of the handle 1614. More specifically, the instrument driver 1618 includes a first drive output 1718a matable with the first drive input 1620a, a second drive output 1718b matable with the second drive input 1620b, a third drive output 1718b matable with the third drive input 1620c, a fourth drive output 1718d matable with the fourth drive input 1620d, a fifth drive output 1718e matable with the fifth drive input 1620e, and a sixth drive output 1718f matable with the sixth drive input 1620f. In some embodiments, as illustrated, the drive outputs 1718a-f may define splines or features designed to mate with corresponding splined receptacles of the drive inputs 1620a-f. Once properly mated, the drive inputs 1620a-f will share axes of rotation with the corresponding drive outputs 1718a-f to allow the transfer of rotational torque from the drive outputs 1718a-f to the corresponding drive inputs 1620a-f. In some embodiments, each drive output 1718a-f may be spring loaded and otherwise biased to spring outwards away from the drive interface 1710. Each drive output 1718a-f may be capable of partially or fully retracting into the drive interface 1710.

In some embodiments, the instrument driver 1618 may include additional drive outputs, depicted in FIG. 17 as a seventh drive output 1718g. The seventh drive output 1718g may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718g. Instead, the driven interface 1712 defines a corresponding recess 1720 (partially occluded) configured to receive the seventh drive output 1718g. In other applications, however, a seventh drive input (not shown) could be included in the handle 1614 to mate with the seventh drive output 1718g, or the surgical tool 1600 might be replaced with another surgical tool having a seventh drive input, which would be driven by the seventh drive output 1718g.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Robotic Instruments with Rack-Based Translation and Firing Transmission

Figure 18A:
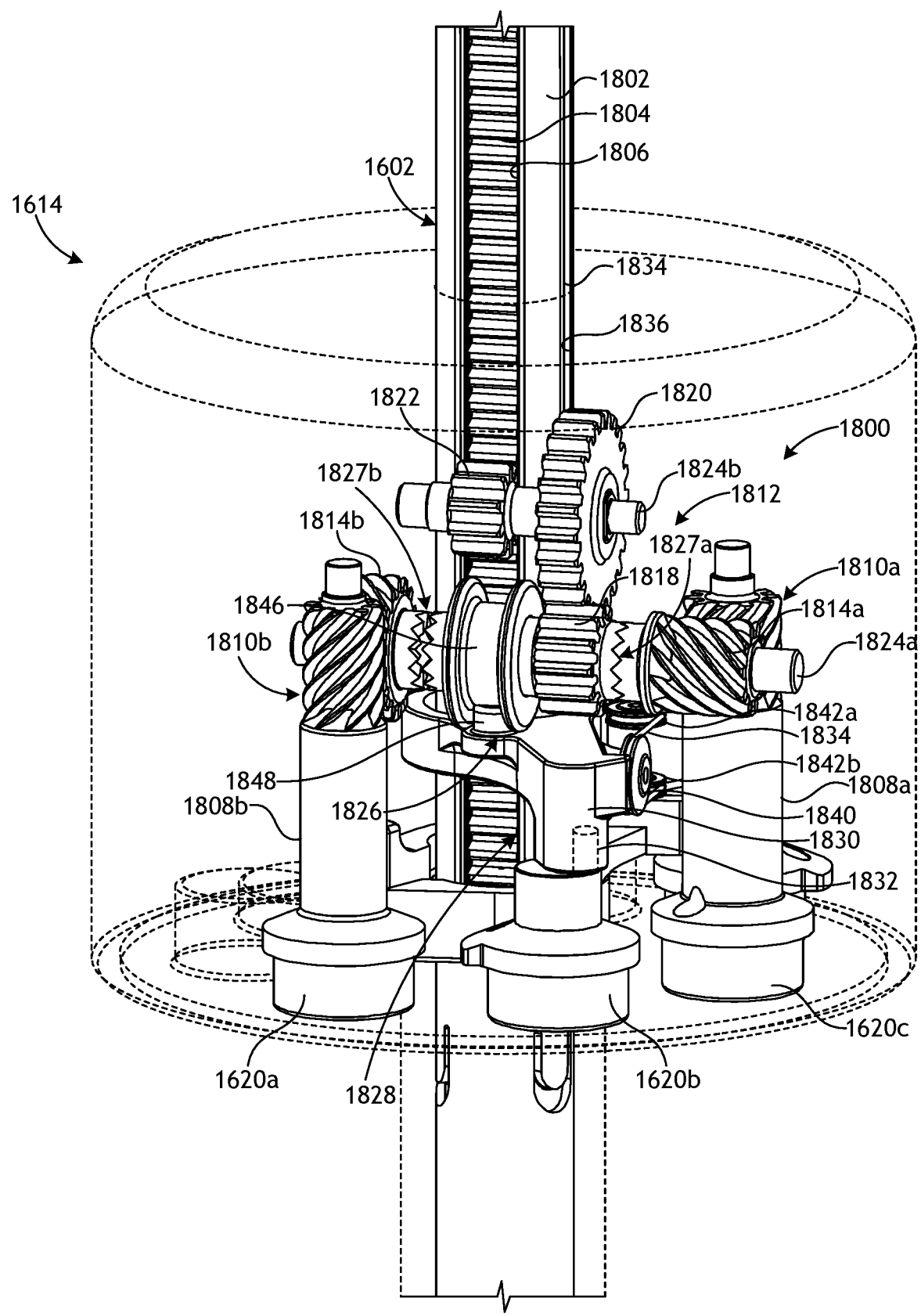
FIGS. 18A and 18B are enlarged isometric views of the handle of FIGS. 16-17 from different side perspectives and depicting an example actuation system, according to one or more embodiments.
Figure 18B:
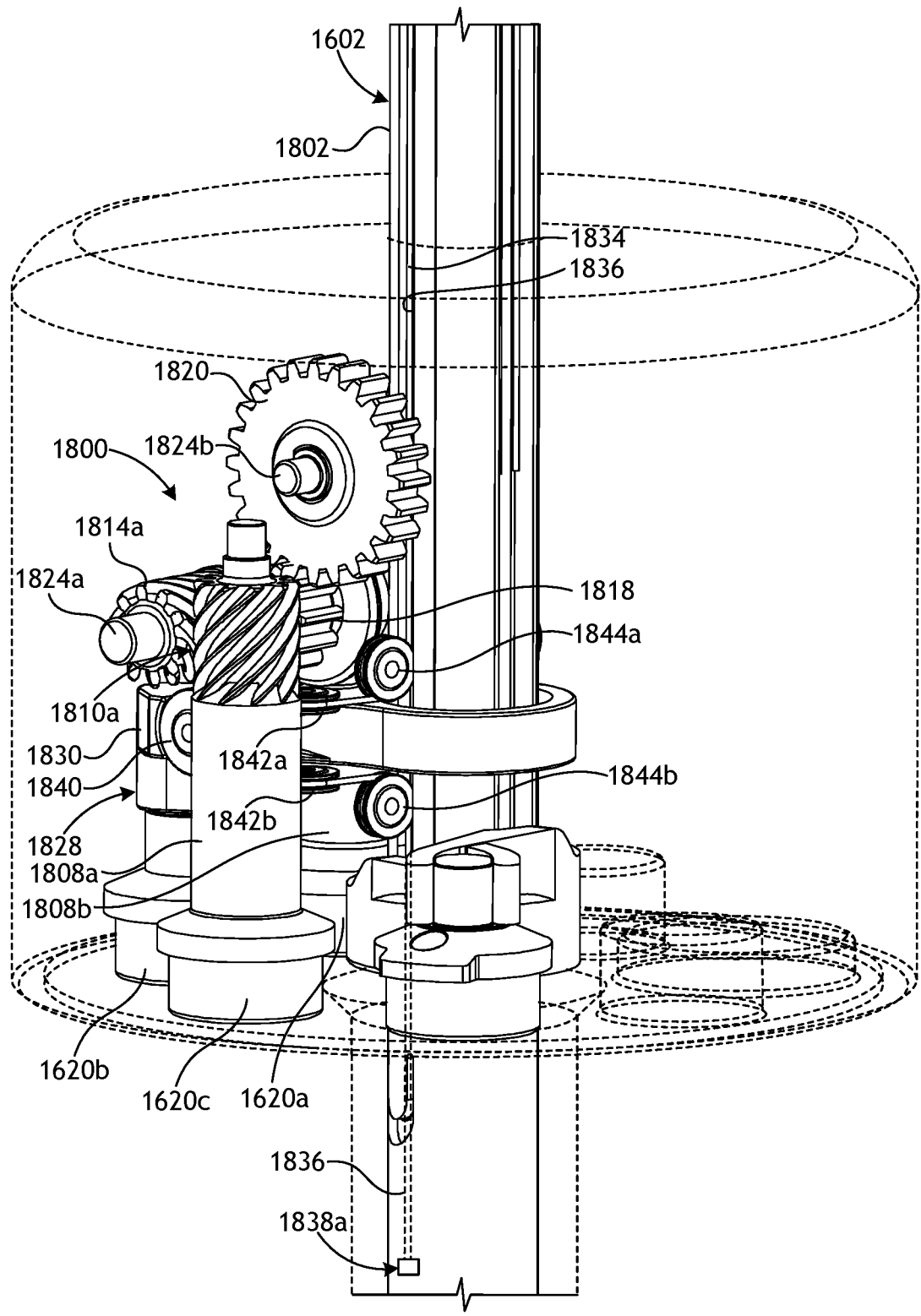

FIGS. 18A and 18B are enlarged isometric views of the handle 1614 from different side perspective views and depicting an example actuation system 1800, according to one or more embodiments of the present disclosure. The outer body of the handle 1614 is shown in phantom (dashed lines) to enable viewing of the internal space within the handle 1614, including the actuation system 1800. Various other actuation systems and component parts of the handle 1614 are omitted in FIGS. 18A-18B for simplicity.

The actuation system 1800 may be operable (actuatable) to carry out a variety of functions (operations) of the surgical tool 1600 (FIG. 16). More specifically, the actuation system 1800 may be actuatable between first and second configurations to perform at least two functions (operations) of the surgical tool 1600. In the first configuration, for example, operation of the actuation system 1800 may cause the shaft 1602 to move relative to the handle 1614 in z-axis translation, and thereby longitudinally advance or retract the end effector 1604 (FIG. 16) arranged at the distal end of the shaft 1602. In the second configuration, however, operation of the actuation system 1800 may secure the shaft 1602 and cause the end effector 1604 to "fire," as generally described above.

As best seen in FIG. 18A, the shaft 1602 may include an outer shaft portion 1802 and a rack 1804 may be at least partially received within a longitudinal channel 1806 defined in the outer shaft portion 1802. As illustrated, the rack 1804 may define gear teeth along at least a portion of its length. As described in more detail below, the rack 1804 may be locked (secured) to or unlocked (released) from the outer shaft portion 1802 (i.e., the shaft 1602) during operation of the actuation system 1800. More specifically, when the actuation system 1800 is in the first configuration, the rack 1804 will be locked to the shaft 1602, such that driving the rack 1804 will cause the shaft 1602 to move relative to the handle 1614 in z-axis translation. In contrast, when the actuation system 1800 is transitioned to the second configuration, the shaft 1602 will be secured against movement and the rack 1804 will be released from the shaft 1602, such that driving the rack 1804 will cause the rack 1804 to move relative to the shaft 1602 and translate (slide) within the channel 1806. The rack 1804 may extend distally and be operatively coupled (either directly or indirectly) to a knife arranged at the end effector 1604 (FIG. 16). Consequently, when the actuation system 1800 is in the second configuration, movement of the rack 1804 relative to the shaft 1602 will cause the knife to advance or retract at the end effector 1604.

As illustrated, the actuation system 1800 includes a first drive shaft or "capstan" 1808a coupled to or forming part of the third drive input 1620c, such that rotation of the third drive input 1620c correspondingly rotates the first capstan 1808a in the same direction. A first helical drive gear 1810a is coupled to or forms part of the first capstan 1808*a* and rotates as the first capstan 1808*a* rotates. The first helical drive gear 1810*a* may be configured to intermesh with and drive a gear train 1812 (best seen in FIG. 18A) that includes one or more interconnected gears configured to ultimately intermesh with and drive the rack 1804. Accordingly, rotation (actuation) of the first capstan 1808*a* may correspondingly drive the rack 1804 via operation of the gear train 1812. In the illustrated embodiment, the gear train 1812 includes a first helical driven gear 1814*a*, a spur drive gear 1818, a spur driven gear 1820, and a pinion gear 1822 (FIG. 18A). While the gear train 1812 is depicted as including four geared components, those skilled in the art will readily appreciate that the gear train 1812 may include more or less than four geared components to drive the rack 1804, without departing from the scope of the disclosure.

In the illustrated embodiment, the first helical driven gear 1814*a* and the spur drive gear 1818 may each be mounted to a first axle 1824*a*. The first helical driven gear 1814*a* may be configured to drive the spur drive gear 1818, as driven by the first helical drive gear 1810*a*. In some embodiments, the spur drive gear 1818 may form an integral part or extension of the first helical driven gear 1814*a*, such that any rotation of the first helical driven gear 1814*a* will correspondingly rotate the spur drive gear 1818. In other embodiments, however, the spur drive gear 1818 may form part of a slip-type clutch 1826 (best seen in FIG. 18A) configured to engage and disengage the first helical driven gear 1814*a* at a first clutch interface 1827*a*. Specifics of the clutch 1826 will be provided in more detail below.

The spur drive gear 1818 may be arranged to drive the spur driven gear 1820, which may be fixed to a second axle 1824*b* such that rotation of the spur driven gear 1820 will correspondingly rotate the second axle 1824*b* in the same direction. The pinion gear 1822 may be coupled to or form part of the second axle 1824*b*, such that rotation of the second axle 1824*b* correspondingly rotates the pinion gear 1822. As illustrated, the gear teeth of the pinion gear 1822 may intermesh with the gear teeth of the rack 1804 such that rotation of the pinion gear 1822 drives or urges the rack 1804 proximally or distally, depending on the rotation direction of the pinion gear 1822. When the actuation system 1800 is in the first configuration, the rack 1804 will be locked to the shaft 1602, such that driving the rack 1804 via rotation of the pinion gear 1822 will move the shaft 1602 relative to the handle 1614 in z-axis translation. When the actuation system 1800 is transitioned to the second configuration, however, the shaft 1602 will be secured against movement and the rack 1804 will be released from the shaft 1602, such that driving the rack 1804 via rotation of the pinion gear 1822 will cause the rack 1804 to move independent of the shaft 1602 and advance or retract a knife arranged at the end effector 1604 (FIG. 16).

The actuation system 1800 may further include a shifting mechanism 1828 operable or otherwise actuatable to transition the actuation system 1800 between the first and second configurations. In the illustrated embodiment, the shifting mechanism 1828 includes an armature 1830 coupled to or forming an integral part of the second drive input 1620*b* such that movement (rotation) of the second drive input 1620*c* correspondingly moves (rotates) the armature 1830. In some embodiments, the armature 1830 may be eccentrically mounted to the second drive input 1620*b*, such as being mounted to a pin 1832 that extends eccentric to a rotation axis of the second drive input 1620*b*. Mounting the armature 1830 to the eccentric pin 1832 may provide a camming effect on the armature 1830 as the second drive input 1620*b* is actuated (rotated). More specifically, rotational input from the second drive input 1620*b* will move the armature 1830 laterally, thus allowing two inputs 1620*a* and 1620*c* with potentially different gear ratios to drive the same rack 1804, as described in more detail below.

The actuation system 1800 may also include a drive member 1834 that extends longitudinally along at least a portion of the shaft 1602. In the illustrated embodiment, the drive member 1834 comprises a cable or wire and, therefore, will be referred to herein as "the drive cable 1834". In other embodiments, however, the drive cable 1834 may comprise any of the other types of drive members mentioned herein. As illustrated, the drive cable 1834 may be received and extend within a groove 1836 defined in the shaft 1602. In other embodiments, however, the drive cable 1834 may alternatively be received within the interior of the shaft 1602 or extend along an exterior surface of the shaft 1602, without departing from the scope of the disclosure.

As best seen in FIG. 18B, a first or "distal" end 1838*a* (FIG. 18B) of the drive cable 1834 may be anchored to the shaft 1602 below (distal to) the handle 1614 and at a distance sufficient to allow the shaft 1602 to translate relative to the handle 1614. As described in more detail below, a second or "proximal" end 1838*b* (see FIG. 19) of the drive cable 1834 may be secured at or near a proximal end of the shaft 1602 and above (proximal to) the handle 1614. The proximal end 1838*b* of the drive cable 1834 may be operatively coupled to a rack locking assembly 1900 (see FIG. 19) and actuation of the shifting mechanism 1828 may cause the drive cable 1834 to act on the rack locking assembly 1900, which may be designed to lock or release the rack 1804 relative to the shaft 1602.

As illustrated, the drive cable 1834 may also extend or be threaded (guided) to the armature 1830 of the shifting mechanism 1828. More specifically, the shifting mechanism 1828 may include a plurality of pulleys through which the drive cable 1834 may be threaded. As illustrated, the shifting mechanism 1828 may include a side accumulator pulley 1840 rotatably mounted to the armature 1830, and may further include a first or "upper" accumulator pulley 1842*a* and a second or "lower" accumulator pulley 1842*b* arranged adjacent the side accumulator pulley 1840 and rotatably coupled to the handle 1614. As best seen in FIG. 18B, the shifting mechanism 1828 may further include a first or "upper" idler pulley 1844*a* and a second or "lower" idler pulley 1844*b*. Similar to the upper and lower accumulator pulleys 1842*a,b*, the upper and lower idler pulleys 1844*a,b* may each be rotatably coupled to the handle 1614.

The upper idler pulley 1844*a* may be arranged and otherwise configured to redirect the drive cable 1834 between the shaft 1602 and the upper accumulator pulley 1842*a*, and the lower idler pulley 1844*b* may be arranged and otherwise configured to redirect the drive cable 1834 between the shaft 1602 and the lower accumulator pulley 1842*b*. The side accumulator pulley 1840 may be arranged to receive and redirect the drive cable 1834 between the upper and lower accumulator pulleys 1842*a,b*. In some embodiments, as illustrated, the upper and lower accumulator pulleys 1842*a,b* may be arranged for rotation in respective parallel planes, while the side accumulator pulley 1840 may be arranged for rotation in a plane that is 90° offset from the parallel planes in order to redirect the drive cable 1834 between the upper and lower accumulator pulleys 1842*a,b*. In one embodiment, for example, the parallel planes of the upper and lower accumulator pulleys 1842*a,b* may be characterized as extending substantially horizontal, and the plane of the side accumulator pulley 1840 may be characterized as extending substantially vertical and otherwise 90° offset from the horizontal planes. In other embodiments, however, the planes of the upper and lower accumulator pulleys 1842a,b and the side accumulator pulley 1840 need not be 90° offset from each other. Moreover, the upper and lower accumulator pulleys 1842a,b need not be arranged for rotation in respective parallel planes, but may alternatively be arranged in non-parallel planes, without departing from the scope of the disclosure.

As mentioned above, the shifting mechanism 1828 may be actuated or operated by rotating the second drive input 1620b, via operation of the second drive output 1718b (FIG. 17). Rotating the second drive input 1620b will correspondingly rotate the armature 1830 in the same direction. Because the distal end 1838a of the drive cable 1834 is anchored to the shaft 1602 distal to the handle 1614, the drive cable 1834 may be drawn (pulled) into the armature 1830 at the upper accumulator pulley 1842a as the armature 1830 rotates. Upon reversing rotation direction of the second drive input 1620b, the armature 1830 will correspondingly rotate in the opposite direction and a length of the drive cable 1834 may correspondingly be paid out (fed) to the shaft 1602 from the upper accumulator pulley 1842a. As discussed below with respect to FIG. 19, drawing in or paying out the drive cable 1834 at the armature 1830 correspondingly acts on the rack locking assembly 1900 of FIG. 19 arranged at or near the proximal end of the shaft 1602, and operation of the rack locking assembly 1900 may lock or release the rack 1804 relative to the shaft 1602, depending on the direction of the drive cable 1834.

In some embodiments, the shifting mechanism 1828 may be decoupled from shaft 1602 insertion. More specifically, the side, upper, and lower accumulator pulleys 1840, 1842a,b and the idler pulleys 1844a,b are able to freely rotate (e.g., "free wheel") and are otherwise not driven during operation of the handle 1614. Consequently, as the shaft 1602 moves longitudinally relative to the handle 1614 in z-axis translation, the drive cable 1834 is able to freely run (course) through the armature 1830 between the upper and lower idler pulleys 1844a,b.

Figure 19:
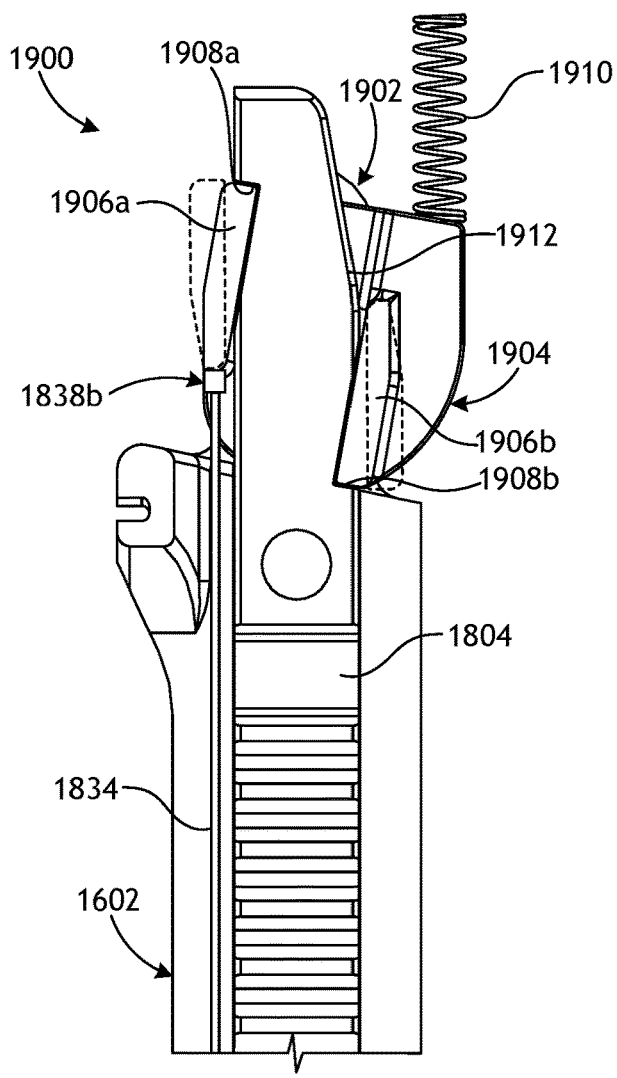
FIG. 19 is an enlarged front view of an example rack locking device, according to one or more embodiments of the disclosure.

FIG. 19 is an enlarged front view of an example rack locking assembly 1900, according to one or more embodiments of the disclosure. As illustrated, the rack locking assembly 1900 may be arranged at or near a proximal end 1902 of the shaft 1602 and may include a latch 1904 pivotably coupled to the shaft 1602 and engageable with the rack 1804. The drive cable 1834 extends proximally from the handle 1614 (FIGS. 18A-18B) to the rack locking assembly 1900, and the proximal end 1838b of the drive cable 1834 may be secured (anchored) to the latch 1904 to enable the latch 1904 to pivot during operation.

The latch 1904, alternately referred to as a "rocker latch," may include or otherwise define various features that are engageable with the rack 1804 at or near its proximal end to lock and release the rack 1804 relative to the shaft 1602. In some embodiments, for example, the latch 1904 may provide a first flange 1906a engageable with a downstop recess 1908a defined on the rack 1804, and a second flange 1906b engageable with an upstop recess 1908b defined on the rack 1804. The downstop and upstop recesses 1908a,b may comprise cutouts in the rack 1804 sized to receive and seat the first and second flanges 1906a,b, respectively. When the first flange 1906a is engaged with the downstop recess 1908a, the rack 1804 will be prevented from moving distally (e.g., down in FIG. 19) relative to the remaining portions of the shaft 1602, and when the second flange 1906b is engaged with the upstop recess 1908b, the rack 1804 will be prevented from moving proximally (e.g., up in FIG. 19) relative to the remaining portions of the shaft 1602. Accordingly, when the first and second flanges 1906a,b are received within the downstop and upstop recesses 1908a,b, respectively, any proximal or distal movement of the rack 1804 will correspondingly move the remaining portions of the shaft 1602.

The latch 1904 may be pivotable between a first or "locked" position, where the first and second flanges 1906a,b are received within the downstop and upstop recesses 1908a,b, respectively, and a second or "released" position, where the first and second flanges 1906a,b are pivoted out of engagement with the downstop and upstop recesses 1908a,b, respectively. The latch 1904 is shown in FIG. 19 in the locked position, and the dashed lines indicate where the first and second flanges 1906a,b may shift to when the latch 1904 is pivoted to the released position.

The latch 1904 may be naturally biased to the locked position. In some embodiments, for example, the rack locking assembly 1900 may further include a compression spring or other deformable elastic member 1910 engageable against the latch 1904 and configured to continuously urge the latch 1904 to the locked position. As will be appreciated, the compression spring 1910 may be replaced with any other type of passive biasing element such as, but not limited to, a torsion spring included at the pivot point of the latch 1904. Actuating the shifting mechanism 1828 (FIGS. 18A-18B), as described above, may apply tension on the drive cable 1834, which will pull distally (i.e., down in FIG. 19) on the latch 1904. The applied tension may overcome the spring force of the compression spring 1910, which will cause the latch 1904 to pivot to the unlocked position and thereby dislodge the first and second flanges 1906a,b from the downstop and upstop recesses 1908a,b, respectively. Actuating the shifting mechanism 1828 in the opposite direction, however, will remove the tension from the drive cable 1834 and thereby allow the latch 1904 to naturally move back to the locked position under the spring force of the compression spring 1910.

When the actuation system 1800 (FIG. 18) is in the first configuration, the latch 1904 will be in the locked position, thus locking the rack 1804 to the shaft 1602. In the locked position, driving the rack 1804 via rotation of the pinion gear 1822 (FIG. 18A), as described above, will move the entire shaft 1602 relative to the handle 1614 (FIGS. 18A-18B) in z-axis translation. In contrast, transitioning the actuation system 1800 to the second configuration will correspondingly pivot the latch 1904 to the released position, thus releasing the rack 1804 from the shaft 1602. In the released position, driving the rack 1804 via rotation of the pinion gear 1822 will cause the rack 1804 to move independent of the shaft 1602 and advance or retract a knife arranged at the end effector 1604 (FIG. 16). After firing the knife, retracting the rack 1804 proximally will allow the latch 1904 to reengage the rack 1804 and thereby revert back to the locked position. In some embodiments, as illustrated, the proximal end of the rack 1804 may provide or otherwise define a tapered edge 1912, which may prove advantageous in guiding the spring-biased second flange 1906b into engagement with the upstop recess 1908b as the rack 1804 moves proximally.

Referring again to FIGS. 18A-18B, the actuation system 1800 may further include a second drive shaft or "capstan" 1808b coupled to or forming part of the first drive input 1620a such that rotation of the first drive input 1620a correspondingly rotates the second capstan 1808b in the same direction. A second helical drive gear 1810b (FIG. 18A) is coupled to or forms part of the second capstan 1808b and rotates as the second capstan 1808b rotates. In some embodiments, the second helical drive gear 1810b may intermesh with and drive the gear train 1812 (best seen in FIG. 18A) when the actuation system 1800 is transitioned to the second configuration. Accordingly, rotation (actuation) of the second capstan 1808b may correspondingly drive the rack 1804 via the gear train 1812 when the actuation system 1800 is in the second configuration.

More specifically, the gear train 1812 may further include a second helical driven gear 1814b (FIG. 18A) mounted to the first axle 1824a and driven by the second helical drive gear 1810b. In some embodiments, as the shifting mechanism 1828 transitions the actuation system 1800 from the first configuration to the second configuration, the clutch 1826 (best seen in FIG. 18A) may be simultaneously moved laterally to disengage the first clutch interface 1827a between the spur drive gear 1818 and the first helical driven gear 1814a. The clutch 1826 may instead be moved laterally to engage a second clutch interface 1827b formed between the spur drive gear 1818 and the second helical driven gear 1814b, and thereby engaging the gear train 1812 with the second helical driven gear 1814b. The clutch 1826 is depicted as a type of "dog clutch," but could alternatively comprise a type of friction clutch, without departing from the scope of the disclosure.

As illustrated, the clutch 1826 may be mounted to and laterally movable along the first axle 1824a. More specifically, the clutch 1826 may include a spool 1846 engageable with a pin 1848 provided by the armature 1830. As the shifting mechanism 1828 transitions from the first configuration to the second configuration, the armature 1830 will correspondingly move the pin 1848 laterally, which will urge the clutch 1826 in the same lateral direction as engaged with the spool 1846. Moving the clutch 1826 laterally will disengage the first clutch interface 1827a at the first helical driven gear 1814a, and instead engage the second clutch interface 1827b at the second helical driven gear 1814b. As will be appreciated, transitioning the actuation system 1800 back to the first configuration will correspondingly cause the clutch 1826 to disengage the second clutch interface 1827b and instead re-engage the first clutch interface 1827a.

Accordingly, when the actuation system 1800 is in the first configuration, as is depicted in FIGS. 18A-18B, the first clutch interface 1827a will be engaged, thus allowing the first helical driven gear 1814a to drive the spur drive gear 1818, which ultimately drives the pinion gear 1822 against the rack 1804. In contrast, and in at least one embodiment, when the actuation system 1800 is transitioned to the second configuration and the clutch 1826 is correspondingly shifted laterally to engage the second clutch interface 1827b, the second helical driven gear 1814b may drive the spur drive gear 1818, ultimately drives the pinion gear 1822 against the rack 1804. As indicated above, the latch 1904 (FIG. 19) may be in the locked position when the actuation system 1800 is in the first configuration, thus locking the rack 1804 to the shaft 1602. Consequently, actuating the third drive input 1620c when the actuation system 1800 is in the first configuration will move the entire shaft 1602 relative to the handle 1614 in z-axis translation. In contrast, transitioning the actuation system 1800 to the second configuration will pivot the latch 1904 to the released position and simultaneously shift the clutch 1826 laterally to engage the second helical driven gear 1814b. In this position, actuating the first drive input 1620a will cause the rack 1804 to move independent of the shaft 1602 and advance or retract a knife arranged at the end effector 1604 (FIG. 16).

Accordingly, actuation of the second drive input 1620b may transition the actuation system 1800 between the first and second configurations. In some embodiments, as discussed above, the third drive input 1620c may be actuatable to drive the rack 1804 for z-axis translation when the actuation system 1800 is in the first configuration, and may further be actuatable to drive the rack 1804 independent of the shaft 1602 for knife firing when the actuation system 1800 is in the second configuration. In other embodiments, however, such as in embodiments that include the clutch 1826, the third drive input 1620c may be actuatable to drive the rack 1804 for z-axis translation when the actuation system 1800 is in the first configuration, but the first drive input 1620a may be actuatable to drive the rack 1804 independent of the shaft 1602 for knife firing. Incorporating the use of both the first and third drive inputs 1620a,c may prove advantageous in incorporating differing engineered gear ratios, thus resulting in differing torque outputs for z-axis translation and knife firing. For example, a lower gear ratio with lower torque may be advantageous for z-axis translation, but a higher gear ratio (e.g., a higher reduction gear train) with more torque may be more appropriate for knife firing. This allows for the use of smaller motors as opposed to a larger motor having sufficient speed and torque to satisfy z-axis insertion speed and knife firing torque requirement. Using smaller motors reduces the mass located near the end of surgical robotic arm, increasing the dynamic response of a given robotic arm. Use of two smaller motors is also advantageous from a thermodynamics standpoint, as smaller motors produce less torque and require less current, thus resulting in less ohmic heating inside the motor. Moreover, smaller motors have less rotational inertia, therefor smaller motors will impart smaller moments to the robotic arm during acceleration or deceleration of said motors.

Figure 20:
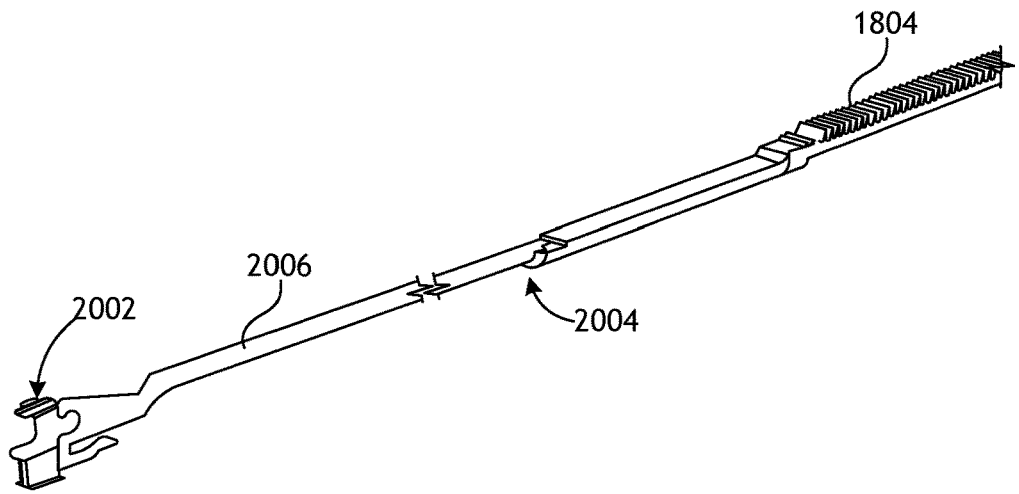
FIG. 20 is an isometric side view of one example of the rack of FIGS. 18A and 19 operatively coupled to a knife, according to one or more embodiments.

FIG. 20 is an isometric side view of one example of the rack 1804 operatively coupled to a knife 2002, according to one or more embodiments. As illustrated, a distal end 2004 of the rack 1804 may be coupled to a firing rod 2006 that extends distally therefrom. The knife 2002 may be coupled to the distal end of the firing rod 2006. In the illustrated embodiment, the rack 1804 is indirectly coupled to the knife 2002 via the firing rod 2006. In other embodiments, however, the rack 1804 may be directly coupled to the knife 2002, without departing from the scope of the disclosure. In either scenario, distal or proximal movement of the rack 1804, as described above, will correspondingly move the knife 2002 in the same direction.

Figure 21:
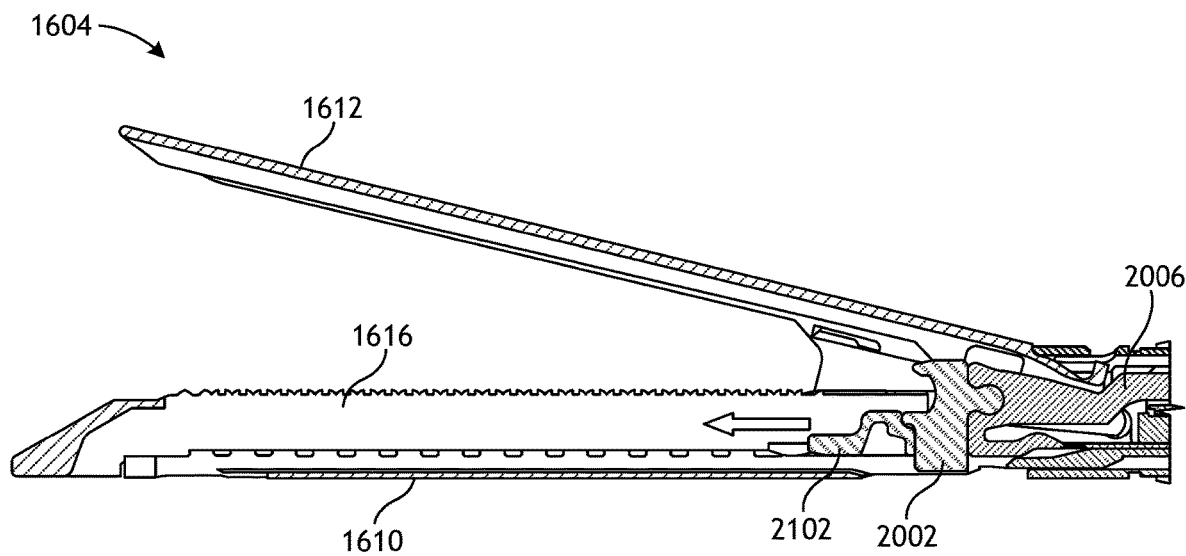
FIG. 21 is an enlarged cross-sectional side view of the end effector of FIG. 16, according to one or more embodiments.

FIG. 21 is an enlarged cross-sectional side view of the end effector 1604, according to one or more embodiments. As mentioned above, the actuation system 1800 (FIGS. 18A-18B) may be operable to cause the end effector 1604 to "fire" when in the second configuration. More specifically, the knife 2002 may be arranged at the end effector 1604, and operation of the actuation system 1800 in the second configuration may cause the knife 2002 to be linearly displaced within the guide track 1616 to cut tissue grasped between the jaws 1610, 1612. The knife 2002 may be operatively coupled to the firing rod 2006, as discussed with reference to FIG. 20, which extends proximally (i.e., to the right in FIG. 21) from the knife 2002 to be coupled to the distal end 2004 (FIG. 20) of the rack 1804 (FIG. 20). Driving the rack 1804, as discussed herein causes the firing rod 2106 to linearly advance and retract and correspondingly advance and retract the knife 2002 within the guide track 1616.

In embodiments where the end effector 1604 comprises a surgical stapler, distally advancing the knife 2002 within the guide track 1616 may simultaneously advance a sled or camming wedge 2004, which engages a plurality of staples (not shown) contained within the lower jaw 1610 (e.g., within a staple cartridge) and urges (cams) the staples into deforming contact with the opposing anvil surfaces (e.g., pockets) provided on the upper jaw 1612. Properly deployed staples help seal opposing sides of the transected tissue.

Figure 22:
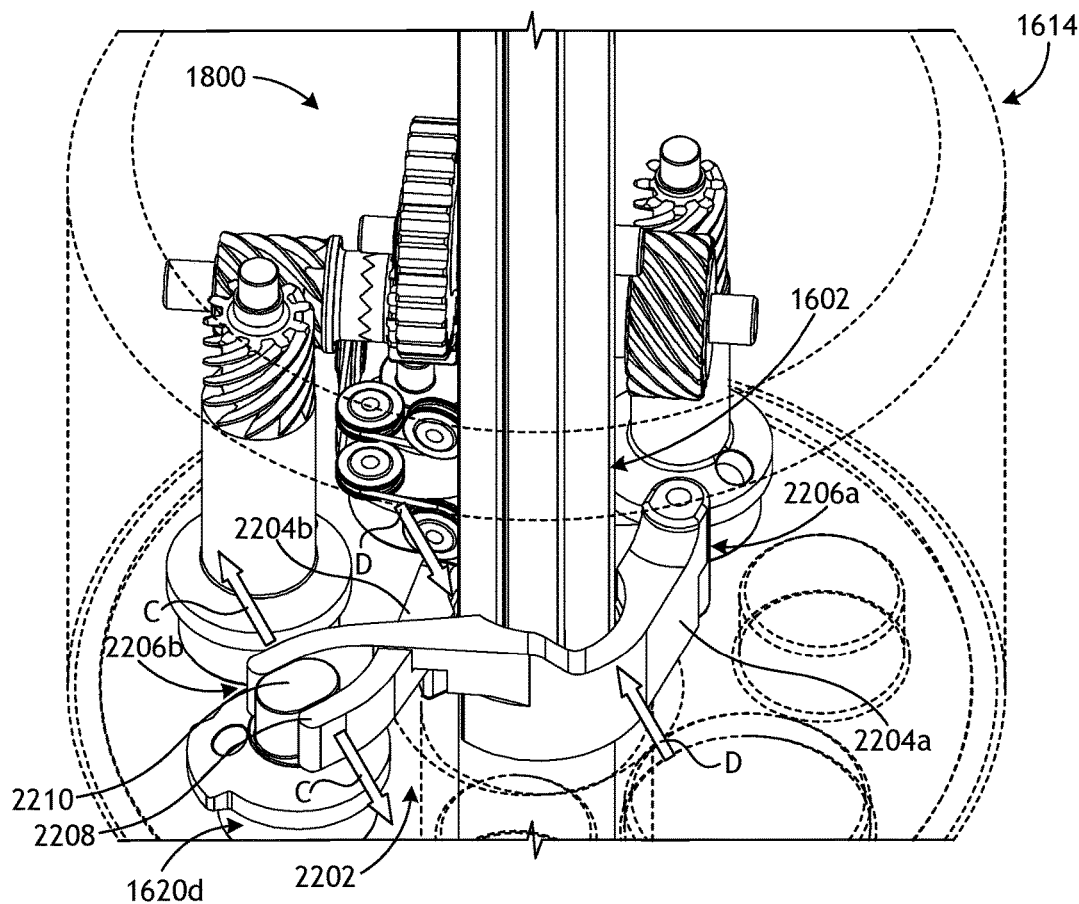
FIG. 22 is another isometric view of the handle and the actuation system of FIGS. 18A-18B, according to one or more embodiments.

FIG. 22 is another isometric view of the handle 1614 and the actuation system 1800 from an alternative perspective, according to one or more embodiments of the present disclosure. Again, the outer body of the handle 1614 is shown in phantom (dashed lines) to enable viewing of the internal space within the handle 1614, including the actuation system 1800. Various other actuation systems and component parts of the handle 1614 are omitted in FIG. 22 for simplicity.

In some embodiments, the actuation system 1800 may further include a shaft locking mechanism 2202 operatively coupled to the fourth drive input 1620d such that actuation (rotation) of the fourth drive input 1620d may operate the shaft locking mechanism 2202 to lock and unlock z-axis translation of the shaft 1602. As illustrated, the shaft locking mechanism 2202 may include first and second caliper actuating arms 2204a and 2204b pivotably coupled to each other at a first end 2206a and engageable with the fourth drive input 1620d at a second end 2206b. At least a portion of each caliper actuating arm 2204a,b may be curved (arcuate) to allow the caliper actuating arms 2204a,b to extend around opposite sides of the shaft 1602. In some embodiments, the first caliper actuation arm 2204a may define a groove 2208 configured to receive a portion of the second caliper actuating arm 2204b in a crossing and sliding engagement during operation. Receiving the second caliper actuating arm 2204b within the groove 2208 may help prevent the caliper actuating arms 2204a,b from separating during operation.

As illustrated, the second ends 2206b of the caliper actuating arms 2204a,b may be engageable with a cam feature 2210 coupled to or forming an integral extension of the fourth drive input 1620d. In the illustrated embodiment, the cam feature 2210 comprises an oblong or oval-shaped pin, but could alternatively comprise any other feature that provides a camming effect when rotated against an adjacent structure. The second ends 2206b of the caliper actuating arms 2204a,b are arranged on opposite sides of the cam feature 2210 such that rotation of the cam feature 2210, as driven by stroke-limited actuation of the fourth drive input 1620d, will correspondingly force the second ends 2206b of the caliper actuating arms 2204a,b away from each other, as indicated by the arrows C. Because of the crossing configuration of the caliper actuating arms 2204a,b, forcing the second ends 2206b away from each other may simultaneously force the caliper actuating arms 2204a,b radially inward, as indicated by the arrows D, and into lateral binding engagement with the shaft 1602. Consequently, a friction-type lock is formed against the shaft 1602 by urging the caliper actuating arms 2204a,b into lateral engagement with the shaft 1602, regardless of the z-axis position of the shaft 1602. Upon reversing the actuation of the fourth drive input 1620d, the gripped engagement of the shaft 1602 with the caliper actuating arms 2204a,b will correspondingly be removed, thus allowing the shaft 1602 to freely translate.

Accordingly, actuating the fourth drive input 1620d may cause the shaft locking mechanism 2202 to mechanically lock and secure the shaft 1602 in place relative to the handle 1614 such that z-axis translation of the shaft 1602 is prevented. In some embodiments, the fourth drive input 1620d may be actuated when the actuation system 1800 is transitioned to the second configuration and poised to drive the rack 1804 (FIGS. 18A and 19) independent of the shaft 1602 to advance or retract the knife 2002 (FIGS. 20-21). In such embodiments, securing the shaft 1602 against z-axis translation may help prevent the shaft 1602 (FIGS. 18A-18B) from inadvertently advancing or retracting along with movement of the rack 1804.

While the shaft locking mechanism 2202 is described and illustrated herein as including the first and second caliper actuating arms 2204a,b operable to move into lateral binding engagement with the shaft 1602 and thereby prevent the shaft 1602 from translating, those skilled in the art will readily appreciate that other designs and systems could equally be employed to lock the shaft 1602 inside the confines of the handle 1614. In one embodiment, for example, a torsion spring may be included that grips the shaft 1602 and is either released or locked when acted on. In other embodiments, a cam lobe could acts directly on the shaft 1602 to stop its axial translation. In yet other embodiments, two thin steel tabs at equal but opposite angles may be included to arrest shaft 1602 motion in both directions and be actuated to release. Accordingly, the shaft locking mechanism 2202 may generally comprise a mechanism in the handle 1614 that acts on the shaft 1602 to arrest axial motion, and that may be released or engaged when acted upon by a particular drive input.

Logic for a Transmission Rack-Based Architecture

Figure 23:
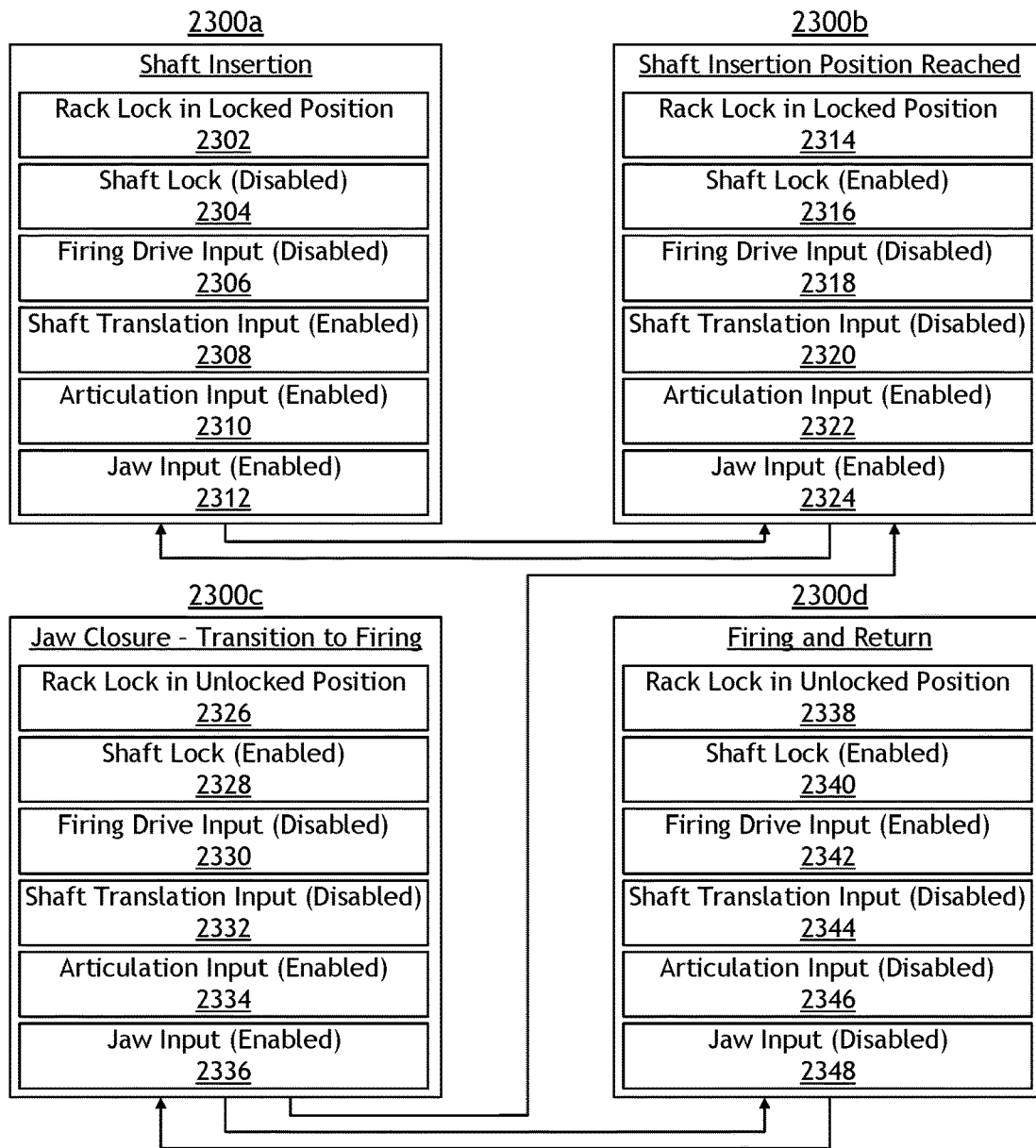
FIG. 23 depicts interconnected logic diagrams for operating the surgical tool 1600 of FIGS. 16-17.

Referring now to FIG. 23, and with continued reference to the actuation system 1800 described in FIGS. 18A-18B, 19, and 22, illustrated are interconnected logic diagrams for operating the surgical tool 1600 of FIGS. 16-17. More specifically, the logic diagrams depict example operational conditions for operating the handle 1614 and the actuation system 1800 in various conditions, as described herein and in accordance with one or more embodiments.

Referring first to the first logic diagram 2300a, depicted are logic and operational conditions for shaft insertion; e.g., z-axis translation of the shaft 1602. To effectively accomplish z-axis translation of the shaft 1602, the latch 1904 is pivoted to the locked position, and thereby securing the rack 1804 to the shaft, as at 2302. The fourth drive input 1620d is also actuated or otherwise disabled to release the shaft locking mechanism 2202 from the shaft 1602, as at 2304, and thereby freeing the shaft 1602 for z-axis translation. The drive input operable to cause firing of the knife 2002 is also disabled, as at 2306. In some embodiments, as discussed above, this may refer to disabling the third drive input 1620b, which is actuatable to drive the rack 1804 and thereby move the knife 2002. In contrast, the drive input operable to cause translation of the shaft 1602 is enabled, as at 2308. As discussed above, the second drive input 1620b may be configured and otherwise actuatable to cause translation of the shaft 1602. During shaft translation, it may also be desired to allow articulation of the end effector 1604 (FIG. 16) and actuation (e.g., opening and closing) of the jaws 1610, 1612 (FIGS. 16-17). Accordingly, the first logic diagram 2300a may further include enabling the drive input operable to cause articulation of the end effector 1604, as at 2310, and enabling the drive input operable to open and close the jaws 1610, 1612, as at 2312. As described herein, in at least one embodiment, the fifth drive input 1620e (FIGS. 16-17) may be actuatable to cause articulation of the end effector 1604, and the sixth drive input 1620f (FIGS. 16-17) may be actuatable to cause the jaws 1610, 1612 to open or close.

Referring to the second logic diagram 2300b, depicted are logic and operational conditions for when a desired shaft insertion position is reached. Once a desired position of the shaft 1602 is reached, the latch 1904 will remain in the locked position, as at 2314, but the fourth drive input 1620d will be actuated to enable the shaft locking mechanism 2202, as at 2316, and thereby secure the shaft 1602 against further z-axis translation. The drive input operable to cause firing of the knife 2002 also remains disabled, as at 2318, and the drive input operable to cause translation of the shaft 1602 is disabled, as at 2320. Once shaft insertion has stopped, however, it may still be desired to allow articulation of the end effector 1604 (FIG. 16) and actuation (e.g., opening and closing) of the jaws 1610, 1612 (FIGS. 16-17). Accordingly, the second logic diagram 2300b may further include maintaining enabled the drive input operable to cause articulation of the end effector 1604, as at 2322, and maintaining enabled the drive input operable to open and close the jaws 1610, 1612, as at 2324.

Referring to the third logic diagram 2300c, depicted are logic and operational conditions for jaw closure and transition to firing. To enable closure of the jaws 1610, 1612 (FIGS. 16-17) and to prepare the end effector 1604 (FIG. 16) for firing, the latch 1904 will be moved to the unlocked position, as at 2326, but the shaft locking mechanism 2202 will remain enabled to continue to prevent z-axis translation of the shaft 1602, as at 2328. The drive input operable to cause firing of the knife 2002 also remains disabled at this point, as at 2330, and the drive input operable to cause translation of the shaft 1602 remains disabled, as at 2332. Since it may still be desired to allow articulation of the end effector 1604 (FIG. 16) and actuation (e.g., opening and closing) of the jaws 1610, 1612 (FIGS. 16-17), the drive input operable to cause articulation of the end effector 1604 will remain enabled, as at 2334, and the drive input operable to open and close the jaws 1610, 1612 will also remain enabled, as at 2336.

Referring to the fourth logic diagram 2300d, depicted are logic and operational conditions for the firing and return of the knife 2002. To enable firing of the knife 2002, the latch 1904 will remain in the unlocked position, as at 2338, but will be transitioned back to the locked position upon return of the knife 2002 and otherwise following the firing process. The shaft locking mechanism 2202 will also remain enabled during knife 2002 firing, as at 2340, to continue to prevent inadvertent translation of the shaft 1602 during firing. The drive input operable to cause firing of the knife 2002 is now enabled, as at 2342, and the drive input operable to cause translation of the shaft 1602 remains disabled, as at 2344. While the knife 2002 fires there is generally no need to articulate the end effector 1604 (FIG. 16) or actuate (e.g., open and close) the jaws 1610, 1612 (FIGS. 16-17). Consequently, the drive input operable to cause articulation of the end effector 1604 will be disabled, as at 2346, and the drive input operable to open and close the jaws 1610, 1612 will also be disabled, as at 2348.

The directional arrows extending between the logic diagrams 2300a-d indicate the order in which the instrument is able to move from one state to another. For example, some states may not be permitted transition to any other state, without first passing through an intermediate state.

Outer Tube Device Function Compensation

Figure 24:
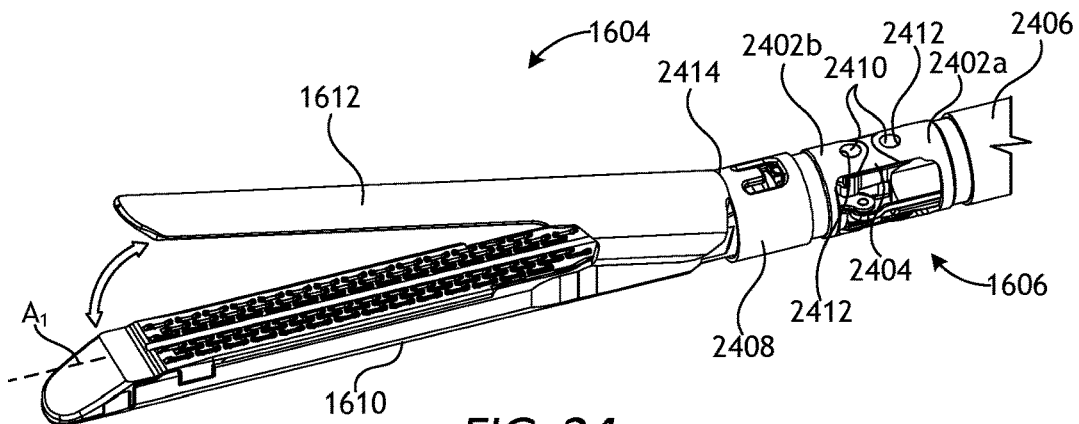
FIG. 24 is an enlarged view of the end effector and the wrist of FIGS. 16-17, according to one or more embodiments.

Referring to FIG. 24, with continued reference to the actuation system 1800 described in FIGS. 18A-18B, 19, and 22, depicted is an enlarged view of the end effector 1604 and the wrist 1606, according to one or more embodiments. As illustrated, the wrist 1606 may include a first or "proximal" clevis 2402a, a second or "distal" clevis 2402b, and a closure link 2404 configured to operatively couple the proximal and distal devises 2402a,b across the wrist 1606. The proximal clevis 2402a may be coupled to or otherwise form part of the distal end of the shaft 1602 and, more particularly, the distal end of a closure tube 2406 that forms an outer portion of the shaft 1602. The distal clevis 2402b may be coupled to or otherwise form part of a closure ring 2408.

In some embodiments, axial movement of the closure tube 2406 along the longitudinal axis $A_1$ may cause the jaws 1610, 1612 of the end effector 1604 to close or open, depending on the longitudinal direction of the closure tube 2406. More specifically, movement of the closure tube 2406 will act on the proximal clevis 2402a in the same axial direction, and the closure link 2404 is configured to transmit the axial load through (across) the wrist 1606 to close or open the jaws 1610, 1612. The closure link 2404 may define a pair of protrusions 2410 configured to mate with corresponding apertures 2412 defined in each of the proximal and distal clevises 2402a,b. The closure link 2404 may transmit the closure load or translation of the closure tube 2406 from the distal clevis 2402b to the proximal clevis 2402a and the closure ring 2408 will correspondingly push or pull on the upper jaw 1612 to open or close the upper jaw 1612. To close the upper jaw 1612, the closure ring 2408 is forced against a shoulder 2414 at or near the back of the upper jaw 1612, which urges the upper jaw 1612 to pivot down and to the closed position. To open the upper jaw 1612, the closure ring 2408 is retracted proximally by retracting the closure tube 2406, and the closure ring 2408 helps pull the upper jaw 1612 back toward the open position. Alternatively, the upper jaw 1612 may be spring loaded and biased to the open position, and retracting the closure ring 2408 removes loading on the shoulder 2414, which allows the spring force to move the upper jaw 1612 to the open position.

In some embodiments, the closure tube 2406 may be advanced or retracted along the longitudinal axis $A_1$ using an actuation system provided in the handle 1614. In such embodiments, for example, the actuation system may include a drive gear engageable with gear teeth provided on the outer surface of the closure tube 2406. Actuating the actuation system will urge the drive gear against the gear teeth of the closure tube 2406 and thereby advance or retract the closure tube 2406 to close or open the jaws 1610, 1612, depending on the movement of the closure tube 2406. Based on the translate and pivot mechanism provided by interaction between the proximal and distal devises 2402a,b and the closure ring 2408, as the closure tube 2406 advances to close the jaws 1610, 1612, the jaws 1610, 1612 will simultaneously advance distally. In some applications, however, advancing the jaws 1610, 1612 distally while closing may not be desired and could be dangerous. For example, when the distal tip of the jaws 1610, 1612 is juxtaposed against an internal organ or vessel of the patient, further distal movement of the jaws 1610, 1612 may cause damage to the organ or vessel.

According to embodiments of the present disclosure, as the closure tube 2406 advances to close the jaws 1610, 1612, the entire shaft 1602 may be simultaneously drawn proximally such that any forward movement of the jaws 1610, 1612 during closure is offset or counteracted by a corresponding equal movement of the shaft 1602 in the opposite direction. For example, when the actuation system is actuated to move the closure tube 2406, the actuation system 1800 of FIGS. 18A-18B may be simultaneously actuated in the first configuration, where the rack 1804 is locked to the shaft 1602 such that driving the rack 1804 causes the entire shaft 1602 to move relative to the handle 1614. In such embodiments, the actuation system 1800 may be operated to move the shaft 1602 proximally to cancel out any distal movement of the jaws 1610, 1612. Furthermore, as the closure tube 2406 retracts proximally to open the jaws 1610, 1612, the actuation system 1800 may be simultaneously operated to move the shaft 1602 distally such that any proximal movement of the jaws 1610, 1612 during opening is offset or counteracted by a corresponding equal movement of the shaft 1602 in the opposite direction. As will be appreciated, this may help ensure that the distal tip of the end effector 1604 remains stationary during closure and opening.

Asymmetric Gear Drive Affecting Knife without Software Decoupling

Figure 25:
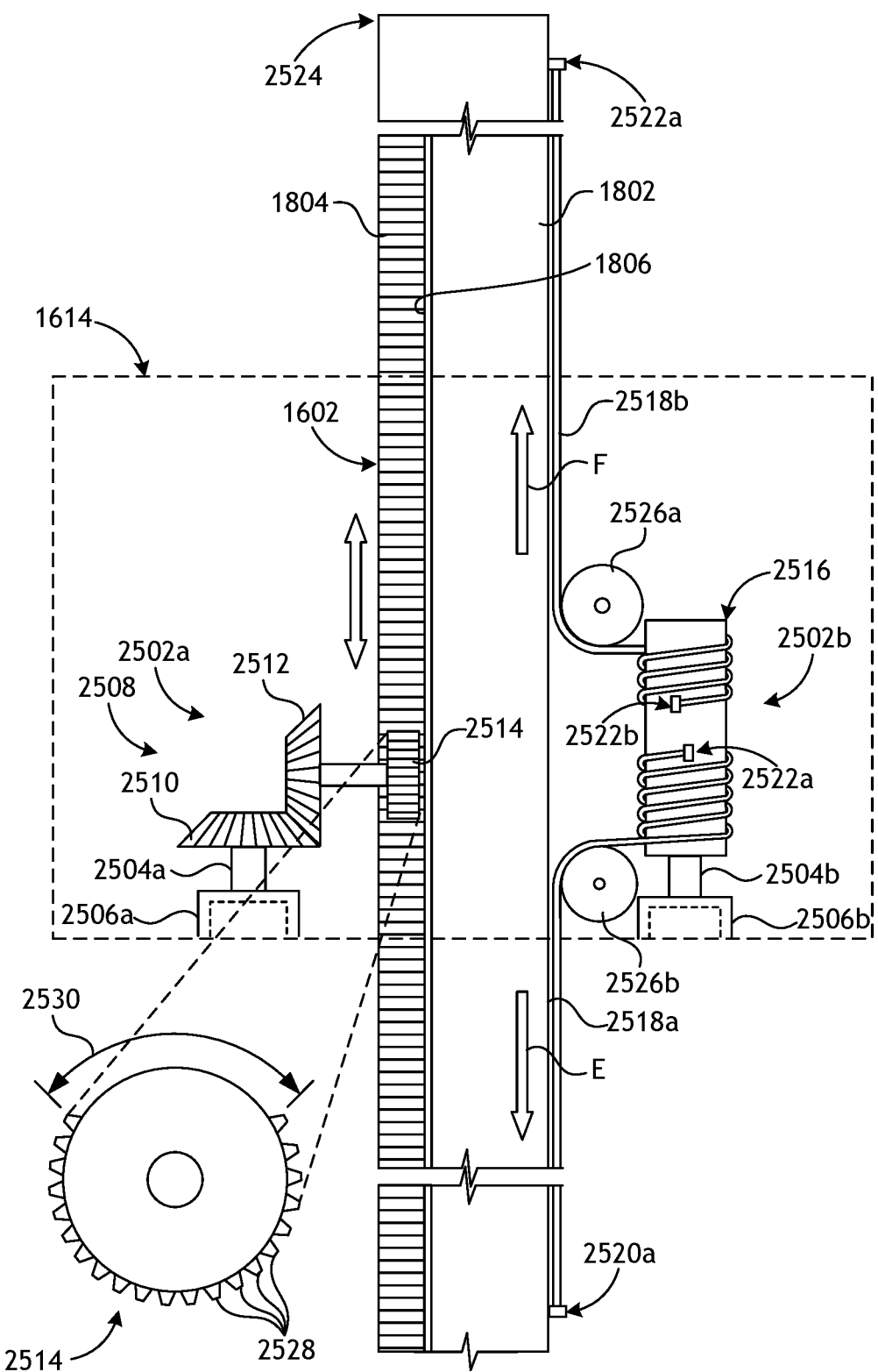
FIG. 25 is an enlarged side view of another embodiment of the handle of FIGS. 16-17, according to one or more embodiments of the present disclosure.

FIG. 25 is an enlarged schematic side view of another embodiment of the handle 1614 of FIGS. 16-17, according to one or more embodiments of the present disclosure. The outer body of the handle 1614 is again shown in phantom (dashed lines) to enable viewing of the internal space and components within the handle 1614. Various actuation systems and component parts of the handle 1614 are omitted in FIG. 25 for simplicity.

The shaft 1602 extends through the handle 1614 and may again include the outer shaft portion 1802 and the rack 1804 at least partially received within the longitudinal channel 1806 defined in the outer shaft portion 1802. Alternatively, the rack 1804 may be arranged outside of the longitudinal channel 1806 or otherwise extend along the exterior of the shaft 1602, without departing from the scope of the disclosure. The rack 1804 may be driven longitudinally relative to the shaft 1602 by engaging gear teeth defined along at least a portion of its longitudinal length. As mentioned above and discussed in more detail below, the rack 1804 may be operatively coupled to the knife 2002 (FIG. 20) arranged at the end effector 1604 (FIG. 16). Consequently, driving the rack 1804 may cause the knife 2002 to advance or retract at the end effector 1604.

As illustrated, the handle 1614 may include a first actuation system 2502a and a second actuation system 2502b. The actuation systems 2502a,b may be operable (actuatable) to carry out a variety of functions (operations) of the surgical tool 1600 (FIG. 16). In the illustrated embodiment, for example, the first actuation system 2502a may be designed and otherwise configured to "fire" the end effector 1604 (FIG. 16), which advances or retracts the knife 2002 (FIG. 20) arranged at the end effector 1604. Moreover, the second actuation system 2502b may be operable to cause the shaft 1602 (including the rack 1804) to move relative to the handle 1614 and thereby longitudinally advance or retract the end effector 1604 in z-axis translation.

The first actuation system 2502a includes a first drive shaft 2504a coupled to or forming part of a first drive input 2506a such that rotation of the first drive input 2506a correspondingly rotates the first drive shaft 2504a in the same direction. The first drive input 2506a may be the same as or similar to any of the drive inputs 1620a-f of FIGS. 16-17 and, therefore, may be matable with any of the drive outputs 1718a-f (FIG. 17) of the instrument driver 1618 (FIGS. 16-17) for actuation (rotation). Rotating the first drive input 2506a may operate or actuate a drive mechanism 2508 that may include any of a variety of interconnected gears, belts, chains, sprockets, etc. configured to ultimately drive the rack 1804. In the illustrated embodiment, the drive mechanism 2508 comprises a type of gear train that includes one or more interconnected (or intermeshed) gears configured to ultimately intermesh with and drive the rack 1804. Accordingly, rotation (actuation) of the first drive shaft 2504a may correspondingly drive the rack 1804 and fire the end effector 1604 (FIG. 16) via operation of the drive mechanism 2508.

In the illustrated embodiment, the drive mechanism 2508 includes a beveled drive gear 2510, a beveled driven gear 2512, and an asymmetric pinion or "sector" gear 2514. The beveled drive gear 2510 intermeshes with and is otherwise arranged to drive the beveled driven gear 2512. The beveled drive gear 2510 is coupled to or forms part of the first drive shaft 2504a such that rotating the first drive shaft 2504a correspondingly rotates the beveled driven gear 2512. Moreover, the sector gear 2514 may be coupled to the beveled driven gear 2512 such that rotating the beveled driven gear 2512 correspondingly rotates the sector gear 2514. Accordingly, actuation of the first actuation system 2502a causes the sector gear 2514 to engage and drive the rack 1804, which may advance or retract the knife 2002 (FIG. 20) operatively coupled to the end of the rack 1804 and arranged at the end effector 1604 (FIG. 16).

The sector gear 2514 may be similar in some respects to the pinion gear 1822 of FIG. 18A and, therefore, may include gear teeth capable of intermeshing with the gear teeth of the rack 1804. Accordingly, selective rotation of the sector gear 2514 may drive the rack 1804 proximally or distally, depending on rotation direction. As described in more detail below, however, the gear teeth may not extend about the entire circumference of the sector gear 2514. Instead, no gear teeth may be provided along a contiguous arcuate length of the sector gear 2514. Accordingly, the sector gear 2514 may be referred to herein as "asymmetric" since its gear teeth are asymmetrically provided about the outer circumference of the gear.

While the drive mechanism 2508 depicted in FIG. 25 includes three geared components, those skilled in the art will readily appreciate that the drive mechanism 2508 may alternatively include more or less than three geared components to drive the rack 1804. Indeed, the depicted drive mechanism 2508 is but one example of a geared system or arrangement designed to drive the rack 1804, and various other designs or configurations of the drive mechanism 2508 may alternatively be incorporated into the first actuation system 2502a, without departing from the scope of the disclosure.

The second actuation system 2502b includes a second drive shaft 2504b coupled to or forming part of a second drive input 2506b such that rotation of the second drive input 2506b correspondingly rotates the second drive shaft 2504b in the same direction. As with the first drive input 2506a, the second drive input 2506b may be the same as or similar to any of the drive inputs 1620a-f of FIGS. 16-17 and, therefore, may be matable with any of the drive outputs 1718a-f (FIG. 17) of the instrument driver 1618 (FIGS. 16-17) for actuation (rotation). Operating the second actuation system 2502b, and thereby rotating the second drive input 2506b, may cause the shaft 1602 (including the rack 1804) to move relative to the handle 1614 and thereby longitudinally advance or retract the end effector 1604 in z-axis translation.

More specifically, as illustrated, the second actuation system 2502b includes a spool 2516 coupled to or forming part of the second drive shaft 2504b such that rotating the second drive shaft 2504b correspondingly rotates the spool 2516 in the same angular direction. The second actuation system 2502b may further include first and second drive members 2518a and 2518b that extend longitudinally along at least a portion of the shaft 1602. In the illustrated embodiment, the drive members 2518a,b comprise cables or wires and, therefore, will be referred to herein as "drive cables". In other embodiments, however, the drive cables 2518a,b may comprise any of the other types of drive members mentioned herein. In some embodiments, the drive cables 2518a,b may be received and extend within corresponding grooves (not shown) defined in the shaft 1602, but may alternatively be received within the interior of the shaft 1602 or extend along the exterior surface of the shaft 1602, without departing from the scope of the disclosure.

As illustrated, the drive cables 2518a,b may each be wrapped around the spool 2516 one or more times. A first or "distal" end 2520a of the first drive cable 2518a may be anchored to the shaft 1602 below (distal to) the handle 1614 and at a distance sufficient to allow the shaft 1602 to translate relative to the handle 1614. A second or "proximal" end 2520b of the first drive cable 2518a may be secured to the spool 2516. In contrast, a first or "proximal" end 2522a of the second drive cable 2518b may be anchored to the shaft 1602 above (proximal to) the handle 1614 and at a distance sufficient to allow the shaft 1602 to translate relative to the handle 1614. In at least one embodiment, the proximal end 2522a may be attached at or near a proximal end 2524 of the shaft 1602. A second or "distal" end 2522b of the second drive cable 2518a may be secured to the spool 2516.

The second actuation system 2502b may further include a first or "upper" idler pulley 2526a and a second or "lower" idler pulley 2526b. The upper and lower idler pulleys 2526a,b may each be rotatably coupled to the handle 1614. The upper idler pulley 2526a may be arranged and otherwise configured to redirect the second drive cable 2518b between the shaft 1602 and the spool 2516, and the lower idler pulley 2526b may be arranged and otherwise configured to redirect the first drive cable 2518a between the shaft 1602 and the spool 2516.

In example operation of the second actuation system 2502b, rotation of the spool 2516 in a first angular direction (e.g., clockwise), via actuation of the second drive input 2506b, will correspondingly pay out (feed) the first drive cable 2518a from the spool 2516 to the shaft 1602, while simultaneously paying in (drawing in) the second drive cable from the shaft 1602 to the spool 2516. Since the distal end 2520a of the first drive cable 2518a is anchored to the shaft 1602 below the handle 1614, and the proximal end 2522a of the second drive cable 2518b is anchored to the shaft 1602 above the handle 1614, paying out the first drive cable 2518a while simultaneously paying in the second drive cable 2518b will cause the shaft 1602 to move distally relative to the handle 1614, as indicated by the arrow E. In contrast, rotation of the spool 2516 in a second angular direction (e.g., counter-clockwise), opposite the first angular direction, will correspondingly pay in (draw in) the first drive cable 2518a from the shaft 1602 to the spool 2516, while simultaneously paying out (feeding) the second drive cable from the spool 2516 to the shaft 1602. Paying in the first drive cable 2518a while simultaneously paying out the second drive cable 2518b will cause the shaft 1602 to move proximally relative to the handle 1614, as indicated by the arrow F.

Referring to the inset, enlarged side view of the sector gear 2514 in FIG. 25, a plurality of gear teeth 2528 may be defined about the outer periphery or circumference of the sector gear 2514. The sector gear 2514, however, may provide or otherwise define a tooth-free zone 2530, which comprises a contiguous arcuate portion of the sector gear 2514 where no gear teeth 2528 are present or found. Accordingly, the sector gear 2514 includes gear teeth 2528 that are asymmetrically formed on the sector gear 2514 and otherwise provided on less than the entire outer circumference (e.g., less than 360°) of the sector gear 2514. In at least one embodiment, the sector gear 2514 may have the same or different geometry of the gear teeth 2528 across the arcuate section of teeth. For example, in some embodiments, the first one or more gear teeth 2528 adjacent to each side of the tooth-free zone 2530 may have a different geometry as compared to the remaining gear teeth 2528 to aid in a smooth transition and engagement with the rack 1804 when the sector gear is rotated.

When the sector gear 2514 is rotated such that the tooth-free zone 2530 faces the rack 1804, no gear teeth 2528 are able to engage the rack 1804, thus effectively decoupling the shaft 1602 from the first actuation system 2502a. Decoupling the shaft 1602 from the first actuation system 2502a allows the shaft 1602 (and the rack 1804) to freely translate relative to the handle 1614 in z-axis translation without the sector gear 2514 binding against the rack 1804 and thereby preventing longitudinal movement.

When it is desired to advance or retract the end effector 1604 (FIG. 16), the first actuation system 2502a may first be configured to rotate the sector gear 2514 such that the tooth-free zone 2530 faces the rack 1804. The second actuation system 2502b may then be operated to freely move the shaft 1602 (and the rack 1804) in z-axis translation without the gear teeth 2528 of the sector gear 2514 engaging (binding against) the rack 1804 and thereby preventing movement of the shaft 1602. In contrast, when it is desired to "fire" the end effector 1604 (FIG. 16) and thereby advance or retract the knife 2002 (FIG. 20) at the end effector 1604, the first actuation system 2502a may be operated to rotate the sector gear 2514 until the gear teeth 2528 engage and drive the rack 1804. If z-axis translation of the shaft 1602 is again desired, the first actuation system 2502a may again be actuated to rotate the sector gear 2514 such that the tooth-free zone 2530 again faces the rack 1804 and decouples the shaft 1602 from the first actuation system 2502a.

In some embodiments, z-axis translation of the shaft 1602 may be locked by disabling the drive output motor operatively coupled to the second drive input 2506b. In other embodiments, or in addition thereto, z-axis translation of the shaft 1602 may be locked or otherwise prevented by engaging the gear teeth 2528 of the sector gear 2514 against the rack 1804. In yet other embodiments, z-axis translation of the shaft 1602 may be prevented by the sector gear 2514 engaging or otherwise operating a lever-type lock (not illustrated).

Belt Shaft Insertion Drive and Sealing

When performing surgical procedures, such as laparoscopic procedures, surgeons commonly incorporate the use of insufflation, which entails introducing a fluid (e.g. carbon dioxide) into an inner cavity (e.g., the abdomen) of a patient to elevate the interior walls of the inner cavity. The fluid is introduced via one or more cannulas inserted into the patient's abdomen and the cannulas are commonly sealed against surgical tool shafts inserted therein to maintain positive pressure inside the patient's body. Various types of seals are used to prevent or minimize air leakage from the patient's body via the tool shafts and thereby achieve a pneumatic seal. These seals, however, are typically designed to accommodate tool shafts with round cross-sections, but it can be difficult to apply the same types of seals to non-circular tool shafts. In particular, pneumatic shaft seals designed to prevent loss of insufflation pressure may be required when using a cable-based architecture compatible with the z-axis insertion, as generally described herein. Seals and seal systems are needed to seal the irregularly-shaped shaft 1602, which may include one or more longitudinal passages or grooves that accommodate various drive members or other structural components.

Figure 26:
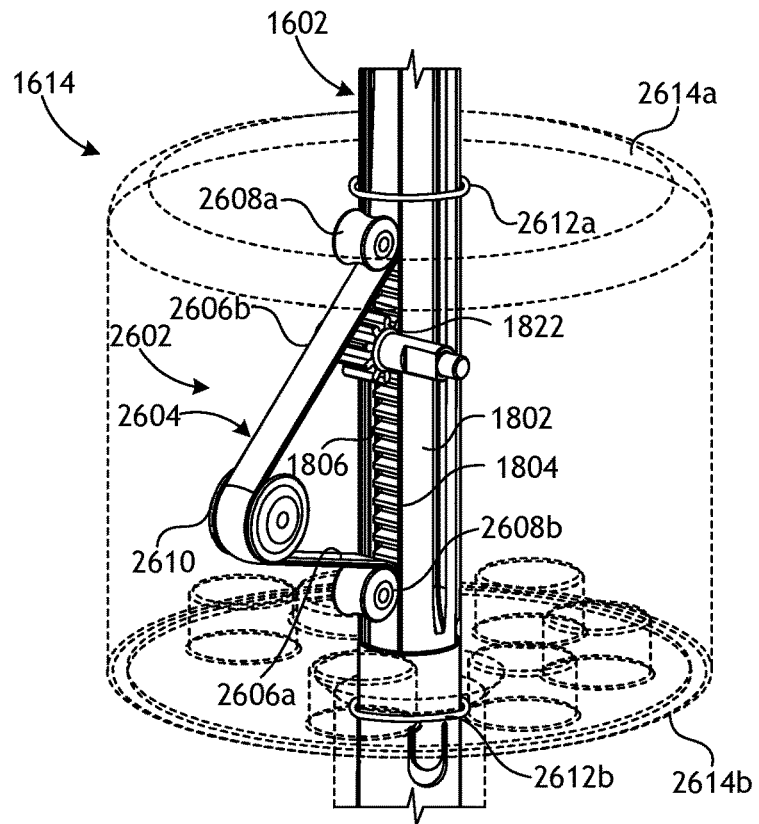
FIG. 26 is an enlarged side view of another embodiment of the handle of FIGS. 16-17, according to one or more additional embodiments of the present disclosure.

FIG. 26 is an enlarged isometric view of another embodiment of the handle 1614 of FIGS. 16-17, according to one or more embodiments of the present disclosure. The outer body of the handle 1614 is again shown in phantom (dashed lines) to enable viewing of the internal space and components within the handle 1614. Moreover, various actuation systems and component parts of the handle 1614 are omitted in FIG. 26 for simplicity.

The shaft 1602 extends through the handle 1614 and may again include the outer shaft portion 1802 and the rack 1804 at least partially received within the longitudinal channel 1806 defined in the outer shaft portion 1802. As described herein, the rack 1804 defines a series of teeth engageable by corresponding gear teeth of a pinion gear, such as the pinion gear 1822. While not depicted in FIG. 26, the pinion gear 1822 may form part of an actuation system designed to rotate the pinion gear 1822 and thereby drive the rack 1804. In at least one embodiment, for example, the pinion gear 1822 may form part of the actuation system 1800 of FIGS. 18A-18B, as described above, but the pinion gear 1822 may alternatively be incorporated into any other actuation system capable of rotating the pinion gear 1822 to drive the rack 1804. Driving the rack 1804, as discussed herein, may cause the entire shaft 1602 to move relative to the handle 1614 in z-axis translation, or may alternatively cause the rack 1804 to move independent of the shaft 1602 and thereby "fire" the end effector 1604 (FIG. 16) arranged at the distal end of the shaft 1602.

The channel 1806 that receives the rack 1804 presents a potential leak path for insufflation pressure to escape from the shaft 1602. To help ensure effective insufflation during operation and otherwise mitigate pressure loss through the shaft 1602, a seal system 2602 may be included in the handle 1614. As illustrated, the seal system 2602 can include a rack seal 2604 that extends along all or a portion of the shaft 1602. The rack seal 2604 is received within the channel 1806 to substantially seal the channel 1806. In the illustrated embodiment, the rack seal 2604 is in the form of an elongate belt that may be made of a compliant material capable of forming a sealed interface such as, but not limited to, an elastomer (e.g., rubber), a plastic, a composite material, or a metal (e.g., thin spring steel). In other embodiments, however, the rack seal 2604 may comprise another type of sealing device or configuration configured to substantially seal along the channel 1806.

In the illustrated embodiment, a distal end of the rack seal 2604 may be anchored to the shaft 1602 at a point distal to the handle 1614, and a proximal end of the rack seal 2604 may be anchored to the shaft 1602 at a point proximal to the handle 1614. As will be appreciated, the distal and proximal ends of the rack seal 2604 may be anchored at distances sufficient to allow the shaft 1602 to translate relative to the handle 1614, as described herein. A bottom surface 2606a of the rack seal 2604 will face the gear teeth of the rack 1804 when the rack seal 2604 is received within the channel 1806. In some embodiments, the bottom surface 2606a may be flat, but could alternatively exhibit an arcuate (widthwise) or undulating shape, without departing from the scope of the disclosure. In at least one embodiment, the bottom surface 2606a may define gear teeth engageable with the gear teeth of the rack 1804, as in more detail discussed below.

When the rack seal 2604 is received within the channel 1806, a top surface 2606b of the rack seal 2604 may be generally aligned with the outer surface of the shaft 1602. In such embodiments, the rack seal 2604 may be received within the channel 1806 and the top surface 2606b may form a flush-fit engagement with the outer surface of the shaft 1602. In some embodiments, for example, the top surface 2606b may be curved, arcuate, or otherwise shaped to match the curvature of the outer surface of the shaft 1602. Such curvature of the top surface 2606b may prove advantageous in allowing the shaft 1602 to be sealed above and below the handle 1614 and across the width of the rack seal 2604.

Within the handle 1614, various rollers may be arranged to redirect the rack seal 2604 out of the channel 1806 and thereby expose the rack 1804 to enable the pinion gear 1822 to interact with the rack 1804. In the illustrated embodiment, for example, the seal system 2602 may further include a first or "upper" idler roller 2608a, a second or "lower" idler roller 2608b, and a redirect roller 2610 interposing the idler rollers 2608a,b. The rollers 2608a,b, 2610 may each be rotatably coupled to the handle 1614 and sized to receive and redirect the rack seal 2604. More specifically, the idler rollers 2608a,b may be arranged and otherwise configured to redirect the rack seal 2604 from the shaft 1602 to the redirect roller 2610 at or near the exit points of the shaft 1602 from the handle 1614. The redirect roller 2610 may be positioned away from the shaft 1602 to expose the rack 1804 for driving. Importantly, however, the idler rollers 2608a,b may also be configured to redirect the rack seal 2604 back to the shaft 1602 at or near the exit points of the shaft 1602 from the handle 1614, and in doing so may help press the rack seal 2604 against the rack 1804 and thereby generate a sealed interface at the channel 1806. Accordingly, as the shaft 1602 translates relative to the handle 1614, the rack seal 2604 is continuously fed through the rollers 2608a,b, 2610 within the handle 1614 and back to the shaft 1602 to provide a sealed interface at the channel 1806.

Because the rack 1804 is exposed within the handle 1614, insufflation pressure may escape the shaft 1602 and feed into the handle 1614. To prevent loss of insufflation pressure to the surrounding environment, the handle 1614 may be at least partially sealed. In one or more embodiments, for example, a first or "upper" dynamic seal 2612a may be coupled to the handle 1614 at or near a first or "proximal" end 2614a of the handle 1614, and a second or "lower" dynamic seal 2612b may be coupled to the handle 1614 at or near a second or "distal" end 2614b of the handle 1614. The dynamic seals 2612a,b may be configured to seal corresponding interfaces between the handle 1614 and the shaft 1602 at the ends 2614a,b of the handle 1614, and otherwise at or near the exit points of the shaft 1602 from the handle 1614. Because of the flush-fit seating of the rack seal 2604 within the channel 1806, the seals 2612 may also be configured to seal against the top surface 2606b of the rack seal 2604. Moreover, the dynamic seals 2612a,b may also be configured to provide a sealed interface during z-axis translation as the shaft 1602. In at least one embodiment, for example, the dynamic seals 2612a,b may comprise lubricated O-rings or another material that allows near frictionless translation.

Figure 27:
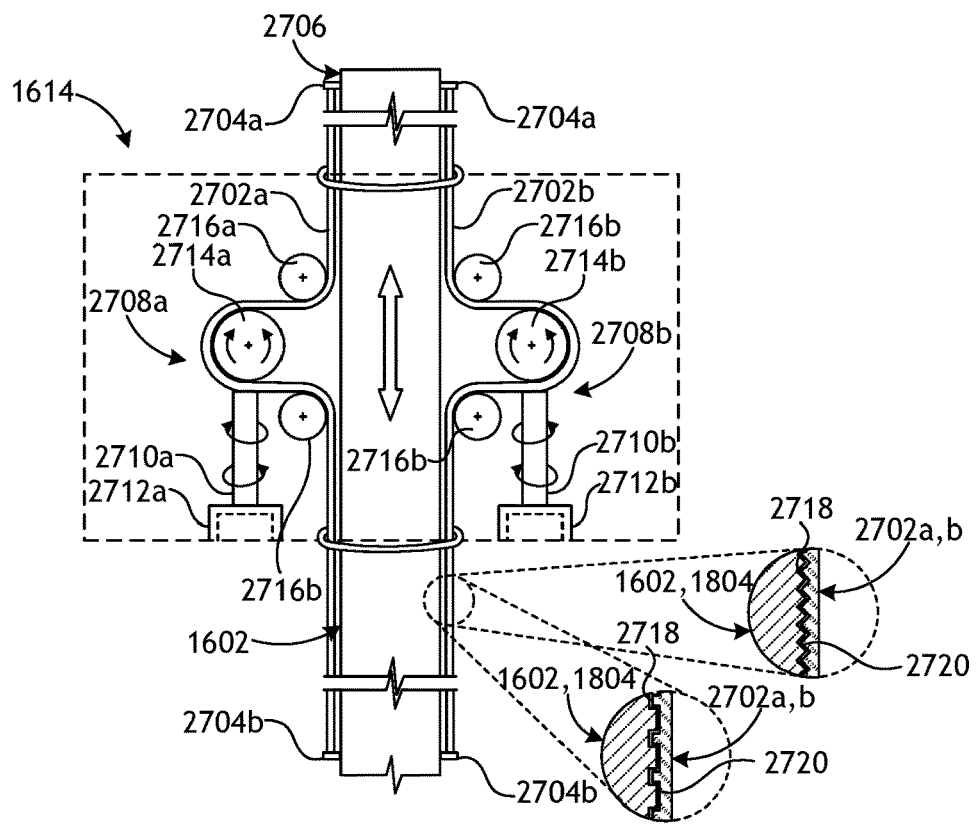
FIG. 27 is an enlarged side schematic view of another embodiment of the handle of FIGS. 16-17, according to one or more additional embodiments of the present disclosure.

FIG. 27 is an enlarged side schematic view of another embodiment of the handle 1614 of FIGS. 16-17, according to one or more additional embodiments of the present disclosure. The outer body of the handle 1614 is again shown in phantom (dashed lines) to enable viewing of the internal space and components within the handle 1614. Moreover, various actuation systems and component parts of the handle 1614 are omitted in FIG. 27 for simplicity.

The shaft 1602 extends through the handle 1614 and may be configured to move relative to the handle 1614 in z-axis translation. In the present embodiment, however, moving the shaft 1602 relative to the handle 1614 may be accomplished using one or more drive belts 2702a and 2702b that extend along all or a portion of the shaft 1602. In the illustrated embodiment, two drive belts 2702a,b are depicted and included on opposite sides of the shaft 1602. Having at least two drive belts 2702a,b may help balance loading across the shaft 1602. Those skilled in the art, however, will readily appreciate that more or less than two drive belts 2702a,b may be incorporated, without departing from the scope of the disclosure.

As illustrated, each drive belt 2702a,b may have a first or "proximal" end 2704a anchored to the shaft 1602 above (proximal to) the handle 1614 and at a distance sufficient to allow the shaft 1602 to translate relative to the handle 1614. In at least one embodiment, the proximal ends 2704a may be attached at or near a proximal end 2706 of the shaft 1602. A second or "distal" end 2704b of each drive belt 2702a,b may be anchored to the shaft 1602 below (distal to) the handle 1614 and at a distance sufficient to allow the shaft 1602 to translate relative to the handle 1614.

The handle 1614 may include first and second actuation systems 2708a and 2708b operable (actuatable) to cause the shaft 1602 to move relative to the handle 1614 and thereby longitudinally advance or retract the end effector 1604 (FIG. 16) in z-axis translation. As illustrated, the first actuation system 2708a includes a first drive shaft 2710a coupled to or forming part of a first drive input 2712a such that rotation of the first drive input 2712a correspondingly rotates the first drive shaft 2710a in the same direction. Similarly, the second actuation system 2708b includes a second drive shaft 2710b coupled to or forming part of a second drive input 2712b such that rotation of the second drive input 2712b correspondingly rotates the second drive shaft 2710b in the same direction. The drive inputs 2712a,b may be the same as or similar to any of the drive inputs 1620a-f of FIGS. 16-17 and, therefore, may be matable with any of the drive outputs 1718a-f (FIG. 17) of the instrument driver 1618 (FIGS. 16-17) for actuation (rotation).

As illustrated, the first actuation system 2708a includes a first drive gear 2714a and the second actuation system 2708b includes a second drive gear 2714b. The first drive belt 2702a interacts with (e.g., extends around) the first drive gear 2714a such that rotating the first drive input 2712a causes the first drive gear 2714a to rotate and thereby drives the first drive belt 2702a. Similarly, the second drive belt 2702b interacts with (e.g., extends around) the second drive gear 2714b such that rotating the second drive input 2712b causes the second drive gear 2714b to rotate and thereby drives the second drive belt 2702b. Each actuation system 2708a,b may also include a first or "upper" idler roller 2716a and a second or "lower" idler roller 2716b. The idler rollers 2716a,b may be rotatably coupled to the handle 1614 and sized to receive and redirect the corresponding drive belts 2702a,b from the shaft 1602, to the respective drive gear 2714a,b, and back to the shaft 1602. In some embodiments, the idler rollers 2716a,b be arranged within the handle 1614 at or near the exit points of the shaft 1602 from the handle 1614 to help hold the drive belts 2702a,b against the shaft 1602.

In example operation, according to at least one embodiment, the actuation systems 2708a,b may be operated to drive the corresponding drive gears 2714a,b in rotation. As the drive gears 2714a,b rotate, the respective drive belts 2702a,b are continuously fed through the idler rollers 2716a,b and along the length of the shaft 1602. Since the drive belts 2702a,b are anchored to the shaft 1602 at proximal and distal ends 2704a,b, movement of the drive belts 2702a,b through the drive gears 2714a,b will cause the shaft 1602 to move relative to the handle 1614 in z-axis translation. As will be appreciated, the shaft 1602 may alternatively be driven in z-axis translation through operation of only one of the actuation systems 2708a,b, without departing from the scope of the disclosure.

Referring now to the enlarged inset graphics provided in FIG. 27, in some embodiments, gear teeth 2718 may be provided or defined on the inner surface of one or both of the drive belts 2702a,b. The gear teeth 2718 may be engageable with corresponding gear teeth 2720 defined on the shaft 1602, or alternatively on the rack 1804. In such embodiments, as the drive gears 2714a,b rotate, the respective drive belts 2702a,b are continuously fed through the idler rollers 2716a,b and along the length of the shaft 1602, which enables intermeshing of the opposing gear teeth 2718, 2720. Accordingly, driving the drive belts 2702a,b will allow the engaged opposing gear teeth 2718, 2720 to drive and move the shaft 1602 relative to the handle 1614 in z-axis translation.

Figure 28:
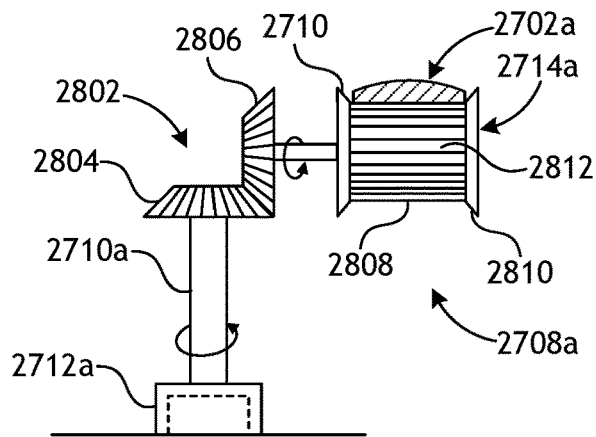
FIG. 28 is a schematic side view of an example of the first actuation system of FIG. 27, according to one or more embodiments.

FIG. 28 is a schematic side view of an example of the first actuation system 2708a of FIG. 27, according to one or more embodiments. While focused on the first actuation system 2708a, the following discussion is equally applicable to the second actuation system 2708b (FIG. 27). As illustrated, the first actuation system 2708a includes the first drive shaft 2710a extending from the first drive input 2712a such that rotation of the first drive input 2712a correspondingly rotates the first drive shaft 2710a. Rotating the first drive input 2712a may operate or actuate a drive mechanism 2802 that may include any of a variety of interconnected gears, belts, chains, sprockets, etc. configured to ultimately drive the rack 1804. In the illustrated embodiment, the drive mechanism 2802 comprises a type of gear train that includes one or more interconnected (or intermeshed) gears extending between the first drive shaft 2710a and the first drive gear 2714a. Accordingly, rotation (actuation) of the first drive shaft 2710a may correspondingly drive the first drive gear 2714a via the drive mechanism 2802 and thereby drive the first drive belt 2702a, which interacts with (e.g., extends around) the first drive gear 2714a.

In the illustrated embodiment, the drive mechanism 2802 includes a beveled drive gear 2804 and a beveled driven gear 2806. The beveled drive gear 2804 intermeshes with and is otherwise arranged to drive the beveled driven gear 2806. The beveled drive gear 2804 is coupled to or forms part of the first drive shaft 2710a such that rotating the first drive shaft 2710a correspondingly rotates the beveled driven gear 2806. Moreover, the first drive gear 2714a may be coupled to the beveled driven gear 2806 such that rotating the beveled driven gear 2806 correspondingly rotates the first drive gear 2714a. Accordingly, actuation of the first actuation system 2708a causes the first drive gear 2714a to engage and drive the first drive belt 2702a and thereby move the shaft 1602 (FIG. 27) relative to the handle 1614 (FIG. 27) in z-axis translation.

While the drive mechanism 2802 depicted in FIG. 28 includes two geared components, those skilled in the art will readily appreciate that the drive mechanism 2802 may alternatively include more or less than two geared components to drive the first drive gear 2714a. Indeed, the depicted drive mechanism 2802 is but one example of a geared system or arrangement designed to drive the first drive gear 2714a, and various other designs or configurations of the drive mechanism 2802 may alternatively be incorporated into the first actuation system 2708a (e.g., mating helical gears), without departing from the scope of the disclosure.

As illustrated, in some embodiments, the first drive gear 2714a may define a depression or trough 2808 sized to receive the first drive belt 2702a. In some embodiments, the trough 2808 may interpose opposing sidewalls 2810 provided by the first drive gear 2714a and the sidewalls 2810 may be laterally offset a sufficient distance to accommodate the width of the first drive belt 2702a. Moreover, the sidewalls 2810 help prevent the first drive belt 2702a from escaping the trough 2808 as the first drive gear 2714a rotates and drives the first drive belt 2702a.

In at least one embodiment, as illustrated, the first drive gear 2714a may have gear teeth 2812 defined thereon within the trough 2808. In such embodiments, the gear teeth 2812 may be configured to intermesh with and engage the gear teeth 2718 (FIG. 27) that may be provided by the first drive belt 2702a. Accordingly, rotating the first drive gear 2714a may drive the first drive belt 2702a via the intermeshed and engaged gear teeth 2718, 2812.

Figure 29:
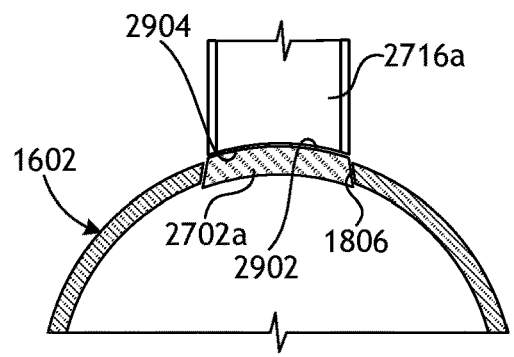
FIG. 29 is a cross-sectional end view of a portion of the shaft and the first drive belt of FIG. 27, according to one or more embodiments.

FIG. 29 is a cross-sectional end view of a portion of the shaft 1602 and the first drive belt 2702a, according to one or more embodiments. While related to first drive belt 2702a, the following discussion is equally applicable to the second drive belt 2702b (FIG. 27). In the illustrated embodiment, the shaft 1602 defines the channel 1806 and the first drive belt 2702a may be received within the channel 1806 to substantially seal the shaft 1602, as generally discussed above. In such embodiments, the first idler roller 2716a may be arranged to help urge and press the first drive belt 2702a into the channel 1806 for a proper seal.

The first drive belt 2702a may be similar in some respects to the rack seal 2604 of FIG. 26. For example, the first drive belt 2702a may provide a top surface 2902 configured to generally align with the outer surface of the shaft 1602 when properly received in the channel 1806. Moreover, in some embodiments, the top surface 2902 may be curved, arcuate, or otherwise shaped to match the curvature of the outer surface of the shaft 1602 such that the top surface 2902 may form a flush-fit engagement with the outer surface of the shaft 1602 when the first drive belt 2702a is properly received in the channel 1806. In some embodiments, the first idler roller 2716a may define an arcuate or concave inner surface 2904 that receives the arcuate or convex outer surface 2902 of the first drive belt 2702a. The inner surface 2904 of the first idler roller 2716a may help deform and urge the first drive belt 2702a into the channel 1806, which may help enhance the sealing capability of the first drive belt 2702a at the channel 1806. Moreover, the inner surface 2904 of the first idler roller 2716a may help shape the first drive belt 2702a to properly fit within the channel 1806 to create a seal.

Figure 30:
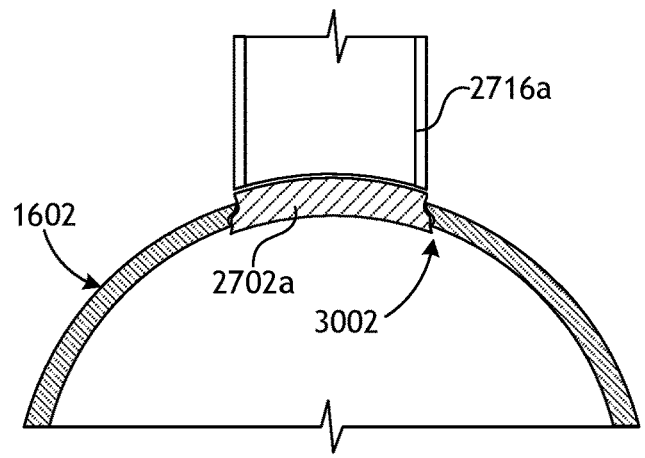
FIG. 30 is a cross-sectional end view of another portion of the shaft and the first drive belt of FIG. 27, according to one or more additional embodiments.

FIG. 30 is a cross-sectional end view of another portion of the shaft 1602 and the first drive belt 2702a, according to one or more additional embodiments. Again, while related to first drive belt 2702a, the following discussion is equally applicable to the second drive belt 2702b (FIG. 27). In the illustrated embodiment, the shaft 1602 defines the channel 1806 and the first drive belt 2702a may be received within the channel 1806 to substantially seal the shaft 1602.

In some embodiments, engagement between the channel 1806 and the first drive belt 2702a may comprise an interlocking engagement 3002 that helps secure the first drive belt 2702a within the channel 1806 and otherwise prevent inadvertent escape. More specifically, in at least one embodiment, the interlocking engagement 3002 may comprise a dovetail interlocking relationship where the first drive belt 2702a may be received within the channel 1806 in a dovetail-shaped interlock. The dovetail interlock between the first drive belt 2702a and the channel 1806 may prove advantageous in enhancing the sealing interface between the two components, but may also help secure the drive belt 2702a within the channel 1806 for operation. Those skilled in the art, however, will readily appreciate that other interlocking designs and configurations may be employed between the first drive belt 2702a and the channel 1806 to help enhance the seal interface between the two components, without departing from the scope of the disclosure. Moreover, in such embodiments, the first idler roller 2716a may be shaped or otherwise configured to force the first drive belt 2702a into the interlocking engagement 3002 and thereby enhance shaft sealing for insufflation and fluid ingress.

FIG. 31 is an enlarged schematic side view of another embodiment of the handle 1614 of FIGS. 16-17, according to one or more additional embodiments of the present disclosure. The outer body of the handle 1614 is again shown in phantom (dashed lines) to enable viewing of the internal space and components within the handle 1614. Moreover, various actuation systems and component parts of the handle 1614 are omitted in FIG. 31 for simplicity. The embodiment of the handle 1614 depicted in FIG. 31 may be similar in some respects to the embodiment of the handle 1614 depicted in FIG. 27, and therefore may be best understood with reference thereto, where like numerals will correspond to like components not described again in detail.

The shaft 1602 extends through the handle 1614 and may be configured to move relative to the handle 1614 in z-axis translation. In the present embodiment, moving the shaft 1602 relative to the handle 1614 may be accomplished using a drive belt 3102 that extends along all or a portion of the shaft 1602. In the illustrated embodiment, the drive belt 3102 may have a first or "proximal" end 3104a anchored to the shaft 1602 above (proximal to) the handle 1614 and at a distance sufficient to allow the shaft 1602 to translate relative to the handle 1614 (e.g., at or near the proximal end 2706 of the shaft 1602). A second or "distal" end 3104b of the drive belt 3102 may be anchored to the shaft 1602 below (distal to) the handle 1614 and at a distance sufficient to allow the shaft 1602 to translate relative to the handle 1614.

The first actuation system 2708a described above in FIG. 27 may be incorporated and otherwise operable (actuatable) to cause the shaft 1602 to move relative to the handle 1614 and thereby longitudinally advance or retract the end effector 1604 (FIG. 16) in z-axis translation. As described above, the first actuation system 2708a includes the first drive shaft 2710a coupled to or forming part of a first drive input 2712a, and the first drive gear 2714a configured to drive the drive belt 3102. More specifically, the drive belt 3102 interacts with (e.g., extends around) the first drive gear 2714a such that rotating the first drive input 2712a causes the first drive gear 2714a to rotate and thereby drives the drive belt 3102. The actuation system 2708a also includes the idler rollers 2716a,b sized to receive and redirect the drive belt 3102 from the shaft 1602, to the drive gear 2714a, and back to the shaft 1602.

In the illustrated embodiment, the drive belt 3102 may include gear teeth 3106 provided or defined on the inner surface of the drive belt 3102. The gear teeth 3106 may be engageable with corresponding gear teeth 3108 defined on the first drive gear 2714a. In such embodiments, as the drive gear 2714a rotates, the drive belt 3102 will be driven via intermeshed engagement between the opposing gear teeth 3106, 3108. Moreover, since the drive belt 3102 is anchored to the shaft 1602 at proximal and distal ends 3104a,b, movement of the drive belt 3102 through rotation of the drive gear 2714*a* will cause the shaft 1602 to move relative to the handle 1614 in z-axis translation.

In other embodiments, however, the gear teeth 3106 may be engageable with corresponding gear teeth (not shown) defined on the outer surface of the shaft 1602, or alternatively on the rack 1804 (FIG. 26). In such embodiments, as the first drive gear 2714*a* rotates, the drive belt 3102 will be continuously fed through the idler rollers 2716*a*,*b* and along the length of the shaft 1602, which enables intermeshing of the opposing gear teeth 3106 on the drive belt 3102 and the exterior of the shaft 1602 or on the rack 1804, which may help drive and move the shaft 1602 relative to the handle 1614 in z-axis translation. Moreover, in embodiments where the drive belt 3102 is received within the channel 1806 (FIG. 26) to engage the rack 1804, the drive belt 3102 may be made of a compliant material capable of forming a sealed interface such as, but not limited to, an elastomer (e.g., rubber), a plastic, or a composite material.

FIGS. 32A and 32B are isometric side and top views, respectively, of an example seal system 3200 that may be incorporated into one or more of the presently disclosed embodiments. In particular, the seal system 3200 may be incorporated into an embodiment that includes the shaft 1602, which may include the outer shaft portion 1802 and the rack 1804 at least partially received within the longitudinal channel 1806 defined in the outer shaft portion 1802. As illustrated, the rack 1804 may define gear teeth 3202 along at least a portion of its length, and the gear teeth 3202 may be engaged by opposing gear teeth of a drive gear (not shown) or a drive belt (not shown) to drive the rack 1804 and thereby cause the shaft 1602 to move relative to the handle 1614 in z-axis translation, or alternatively the rack 1804 may be driven independent of the shaft 1602 and translated within the channel 1806 to cause a knife to advance or retract (e.g., "fire").

The seal system 3200 may be included in the handle 1614 of any of the embodiments described herein that include the rack 1804. As the shaft 1602 moves in z-axis translation or as the rack 1804 moves relative to the shaft 1602, the seal system 3200 remains stationary with the handle 1614 and provides a sealed interface between the handle 1614 and the shaft 1602.

As illustrated, the seal system 3200 may include a roller seal 3204 and a stationary flange seal 3206. The roller seal 3204 may be arranged to engage the rack 1804. More particularly, the roller seal 3204, alternately referred to as a "rotating labyrinth seal," may be freely rotatable and include gear teeth 3208 configured to intermesh with the gear teeth 3203 of the rack 1804. Consequently, as the shaft 1602 or the rack 1804 translate during operation, the roller seal 3204 will roll in contact along the rack 1804 as the opposing gear teeth 3202, 3208 interact with each other. The roller seal 3204 may provide a sealed interface against the rack 1804 that helps seal the exposed channel 1806. In some embodiments, for example, the roller seal 3204 may be made of a compliant material, such as a soft elastomer or a foam that is able to roll in contact with the mating teeth 3202 of the rack 1804, while simultaneously providing a sealed interface.

The flange seal 3206 extends partially around the outer circumference of the shaft 1602 and extends radially outward therefrom to provide a sealed interface at the outer surface of the shaft 1602. The flange seal 3206 may also extend to and slidingly engage the opposing lateral sides of the roller seal 3204. In some embodiments, the flange seal 3206 may comprise an elastomeric skirt seal, but could alternatively comprise any other type of seal capable of sealing about the outer circumference of the shaft 1602 and slidingly engaging the lateral sides of the roller seal 3204. As the shaft 1602 translates during operation, the flange seal 3206 may dynamically seal against the outer surface of the shaft 1602, and may also dynamically seal against the lateral sides of the roller seal 3204 as the roller seal 3204 rolls in contact along the moving rack 1804.

Pneumatic Seal Cartridge for Robotic Vessel Sealer

Figure 33:
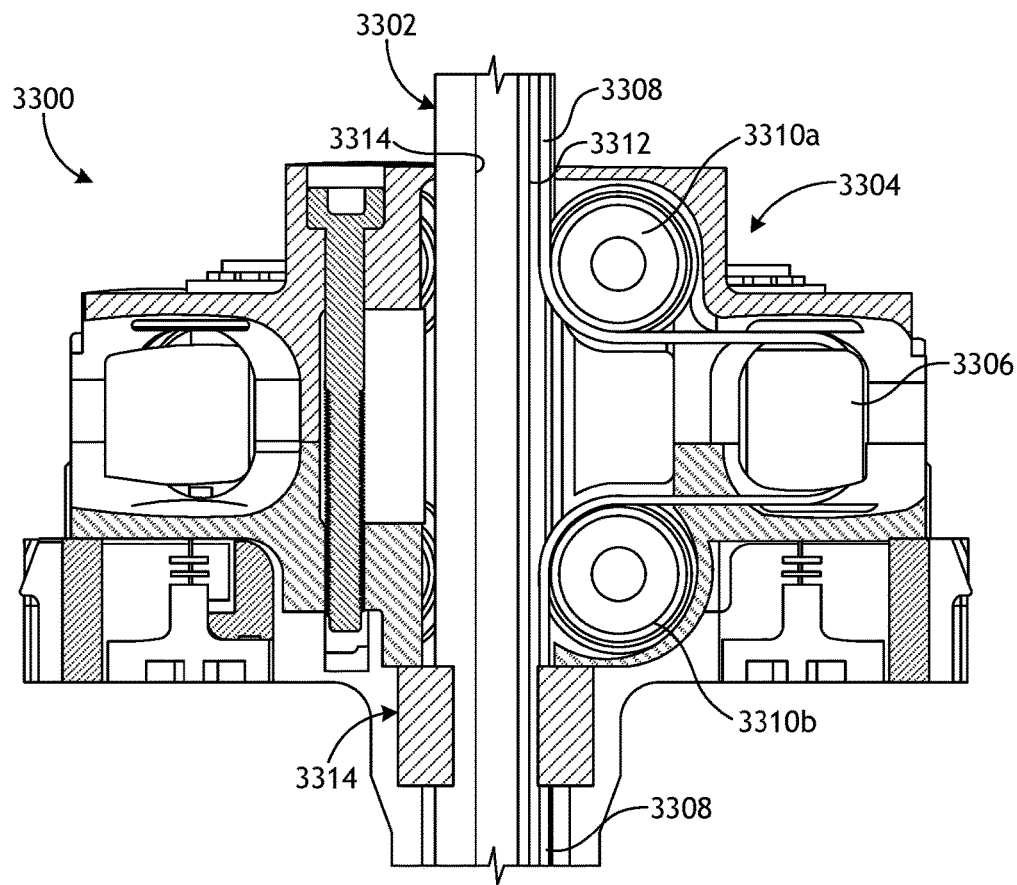
FIG. 33 is a partial cross-sectional side view of an example handle, according to one or more embodiments.

FIG. 33 is a partial cross-sectional side view of an example handle 3300, according to one or more embodiments. The handle 3300 may be similar in some respects to the handle 1614 described herein, and may thus be incorporated into the surgical tool 1600 of FIGS. 16-17. As illustrated, an elongate shaft 3302 may extend through the handle 3300 and may be configured for z-axis translation relative to the handle 3300. To accomplish this, the handle 3300 may further include an actuation system 3304 that includes a spool 3306 and one or more drive cables 3308 (two shown) at least partially wrapped around the spool 3306 and extending longitudinally along a portion of the shaft 3302. The actuation system 3304 further includes upper and lower idler pulleys 3310*a* and 3310*b* rotatably coupled to the handle 3300 and arranged to redirect the drive cables 3308 between the shaft 3302 and the spool 3306.

In the illustrated embodiment, the drive cables 3308 are received and extend within a groove 3312 defined along all or a portion of the length of the shaft 3302. The groove 3312 may be accompanied by various other longitudinal passages or grooves 3314 defined longitudinally along the shaft 3302 to accommodate other types of cables or drive members. The grooves 3312, 3314 result in the shaft 3302 exhibiting a non-circular cross section created by the longitudinal passages that could allow insufflation air to leak from a patient. To prevent insufflation air leakage, the handle 3300 may further include one or more seal cartridges 3314 (one shown) configured to seal about the non-circular cross section of the shaft 3302.

In the illustrated embodiment, the seal cartridge 3314 is arranged about the shaft 3302 at or near the distal (bottom) end of the handle 3300. While not shown, a second seal cartridge (not shown) may be arranged about the shaft 3302 at or near the proximal (top) end of the handle 3300. As illustrated, the drive cable 3308 extends through the seal cartridge 3314, which is configured to seal about the drive cable 3308.

Figure 34A:
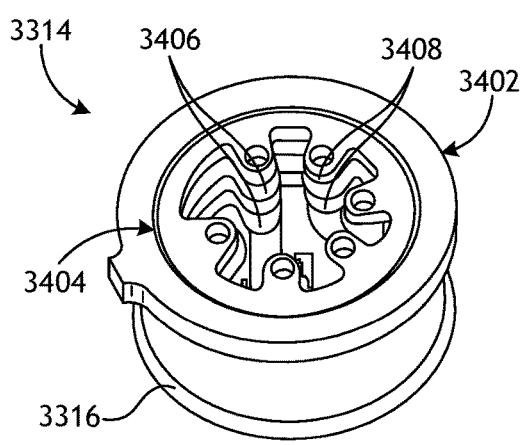
FIGS. 34A and 34B are isometric and top views, respectively, of an example of the seal cartridge of FIG. 33, according to one or more embodiments.
Figure 34B:
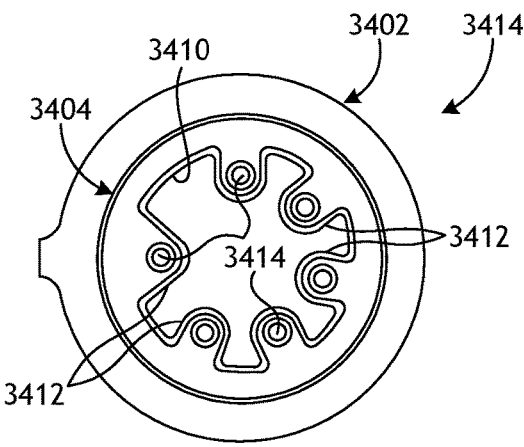

FIGS. 34A and 34B are isometric and top views, respectively, of an example of the seal cartridge 3314 of FIG. 33, according to one or more embodiments. As illustrated, the seal cartridge 3314 may include a housing 3402 having a seal membrane 3404 arranged within the housing 3402. The housing 3402 may be made of a rigid or semi-rigid material such as, but not limited to, a metal (e.g., stainless steel, aluminum, titanium, etc.), a polymer, a composite material, or any combination thereof. In the illustrated embodiment, the cross-sectional shape of the housing 3402 is circular, but could alternatively comprise other shapes, such as oval, ovoid, polygonal (e.g. triangular, rectangular, etc.), without departing from the scope of the disclosure.

The seal membrane 3404 has a generally circular outer circumference (perimeter) generally matable with the inner surface of the housing 3402. As best seen in FIG. 34A, in some embodiments, the seal membrane 3404 may comprise one or more flexible seals 3406 vertically stacked with one or more structure plates 3408. The flexible seals 3406 may be made of any compliant sealing material including, but not limited to, an elastomer (rubber), a polymer, or a composite material. In at least one embodiments, the flexible seals 3406 may contain at least one fiber or filler for the purpose of mechanical reinforcement, lubricity, or to act as a wear modifier. Moreover, the seals 3406 may be impregnated with synthetic oils or organic compounds to increase lubricity and reduce static or kinetic friction. As will be appreciated, decreasing friction helps with robotic controls and accuracy. In contrast, the structure plates 3408 may be made of a rigid or semi-rigid material, such as a metal, a plastic, or a composite material. In some embodiments, the various layers of the seals 3406 may comprise materials of varying (different) durometers. Similarly, the various layers of the structure plates 3408 may comprise materials of varying (different) durometers.

The seals 3406 and the structure plates 3408 may be die cut and stacked in assembling the seal membrane 3404. In at least one embodiment, once the seals 3406 and the structure plates 3408 are stacked, the housing 3402 may be overmolded onto the assembled seal membrane 3404. In the illustrated embodiment, two flexible seals 3406 are alternatingly stacked with two structure plates 3408, but more or less than two of each may be provided, without departing from the scope of the disclosure.

As best seen in FIG. 34B, the seal membrane 3404 defines an arcuate shaft surface 3410 and one or more nubs or projections 3412 extending radially inward from the shaft surface 3410. The projections 3412 may be configured to be received within corresponding passages or grooves defined longitudinally in a tool shaft, such as the grooves 3312, 3314 (FIG. 33) of the shaft 1602 (FIG. 33), thus helping to reduce the risk of air leakage from a patient during surgery. As illustrated, each projection 3412 may also define an aperture 3414 configured to receive a longitudinally-extending drive member of the surgical tool, such as the drive cables 3308 (FIG. 33). As the shaft 1602 translates relative to the handle 3300 (FIG. 33), the projections 3412 may be configured to translate (slide) within the grooves 3312, 3314 while receiving corresponding drive members, thereby creating a sliding linear seal for instrument shaft motion. The seal membrane 3404 directly contacts at least one surface of the tool shaft and at least one cable, tube, or drive rod passing through or parallel to the tool shaft axis for the purpose of creating a pneumatic seal. Any cable, tube, or drive rod contacting at least one surface of the seal membrane 3404, and passing through the handle 3300 (FIG. 33) to a distal end effector, does so for the purpose of actuating the end effector.

One skilled in the art will appreciate that while the seal cartridge 3314 is shown with a plurality of projections 3412 that are rounded and spaced substantially symmetrically around an inner perimeter, the inner portion of the seal cartridge 3314 can assume other shapes as well, so long as the molding process substantially matches the interior of the seal cartridge 3314 to the outer surface of the instrument shaft 3302.

As best seen in FIG. 34A, the seal cartridge 3314 may contain at least one outer seal 3316 configured to form a sealed interface between the housing 3402 and an inner surface of the handle 3300 (FIG. 33), such as in the nose cone of the instrument. The outer seal 3316 may comprise, for example, an elastomeric O-ring, flange, or other commonly available sealing member. At least one surface of the handle 3300 may contact the outer seal 3316 for the purpose of forming a pneumatic seal.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
   a handle providing a first drive input and a second drive input;
   an elongate shaft extendable through the handle and having an end effector arranged at a distal end thereof; and
   a rack extending along a portion of the shaft and operatively coupled to a knife located at the end effector,
   wherein actuation of the first drive input transitions the rack between a locked configuration, where the rack is locked to the shaft, and a released configuration, where the rack is released from the shaft, wherein actuation of the second drive input with the rack in the locked configuration drives the rack and causes z-axis translation of the shaft through the handle, and wherein actuation of the second drive input with the rack in the released configuration drives the rack relative to the shaft and thereby advances or retracts the knife at the end effector.

2. The robotic surgical tool of claim 1, further comprising an actuation system housed within the handle and including:

a shifting mechanism operatively coupled to the first drive input such that actuation of the first drive input transitions the rack between the locked configuration and the released configuration; and a capstan coupled to the second drive input and including a drive gear engageable with a gear train that intermeshes with the rack.

3. The robotic surgical tool of claim 1, further comprising:

a rack locking assembly arranged at a proximal end of the shaft and including a latch pivotably coupled to the shaft and engageable with the rack; and a drive cable extending from the shifting mechanism and fixed to the latch, wherein transitioning the actuation system to the second configuration places tension on the drive cable and thereby pivots the latch from a locked position, where the latch secures the rack to the shaft, to a released position, where the latch is released from the rack and allows the rack to move relative to the shaft.

4. The robotic surgical tool of claim 3, wherein the latch is spring biased to the locked position.

5. The robotic surgical tool of claim 3, wherein a distal end of the drive cable is anchored to the shaft distal to the handle and the drive cable extends through one or more pulleys included in the shifting mechanism, and wherein actuation of the first drive input shifts the shifting mechanism and thereby draws in or pays out a portion of the drive cable.

6. The robotic surgical tool of claim 1, further comprising a shaft locking mechanism operatively coupled to a third drive input of the handle, wherein actuation of the third drive input causes the shaft locking mechanism to engage and prevent the shaft from moving in z-axis translation.

7. The robotic surgical tool of claim 6, wherein the shaft locking mechanism comprises first and second caliper actuating arms pivotably coupled to each other at a first end and engageable with the third drive input at a second end, and wherein actuation of the third drive input forces the first and second caliper actuating arms into lateral binding engagement with the shaft.

8. A robotic surgical tool, comprising:

a handle providing a first drive input, a second drive input, and a third drive input;

an elongate shaft extendable through the handle and having an end effector arranged at a distal end thereof;

a rack extending along a portion of the shaft and operatively coupled to a knife located at the end effector;

an actuation system housed within the handle and including:

a shifting mechanism operatively coupled to the first drive input such that actuation of the first drive input transitions the actuation system between a first configuration, where the rack is locked to the shaft, and a second configuration, where the rack is released from the shaft;

a first capstan coupled to the second drive input and including a first drive gear engageable with a gear train that intermeshes with the rack when the actuation system is in the first configuration; and a second capstan coupled to the third drive input and including a second drive gear engageable with the gear train when the actuation system is in the second configuration, wherein actuation of the second drive input with the actuation system in the first configuration drives the rack and causes z-axis translation of the shaft through the handle, and wherein actuation of the third drive input with the actuation system in the second configuration drives the rack relative to the shaft and thereby advances or retracts the knife at the end effector.

9. The robotic surgical tool of claim 8, further comprising:

a rack locking assembly arranged at a proximal end of the shaft and including a latch pivotably coupled to the shaft and engageable with the rack; and a drive cable extending from the shifting mechanism and fixed to the latch, wherein transitioning the actuation system to the second configuration places tension on the drive cable and thereby pivots the latch from a locked position, where the latch secures the rack to the shaft, to a released position, where the latch is released from the rack and allows the rack to move relative to the shaft.

10. The robotic surgical tool of claim 9, wherein the latch is spring biased to the locked position.

11. The robotic surgical tool of claim 9, wherein a distal end of the drive cable is anchored to the shaft distal to the handle and the drive cable extends through one or more pulleys included in the shifting mechanism, and wherein actuation of the first drive input shifts the shifting mechanism and thereby draws in or pays out a portion of the drive cable.

12. The robotic surgical tool of claim 8, further comprising a shaft locking mechanism operatively coupled to a fourth drive input of the handle, wherein actuation of the fourth drive input causes the shaft locking mechanism to engage and prevent the shaft from moving in z-axis translation.

13. The robotic surgical tool of claim 12, wherein the shaft locking mechanism comprises first and second caliper actuating arms pivotably coupled to each other at a first end and engageable with the fourth drive input at a second end, and wherein actuation of the fourth drive input forces the first and second caliper actuating arms into lateral binding engagement with the shaft.

14. The robotic surgical tool of claim 8, further comprising:

a first driven gear mounted to an axle and engageable with the first drive gear;

a second driven gear mounted to the axle and engageable with the second drive gear; and a clutch interposing the first and second drive gears and laterally movable with the shifting mechanism between the first and second driven gears, wherein the clutch engages a first clutch interface at the first driven gear when the actuation system is in the first configuration and thereby allows the first drive gear to drive the rack via the gear train, and wherein the clutch engages a second clutch interface at the second driven gear when the actuation system is in the second configuration and thereby allows the second drive gear to drive the rack via the gear train.

15. The robotic surgical tool of claim 14, wherein the clutch includes a spool engageable with a pin provided by the shifting mechanism, and wherein transitioning the actuation system between the first and second configurations moves the clutch between the first and second clutch interfaces via the engaged spool and pin.

\* \* \* \* \*